(12) United States Patent
Ghigo et al.

(10) Patent No.: US 7,825,090 B2
(45) Date of Patent: Nov. 2, 2010

(54) USE OF GHRELIN AND UNACYLATED GHRELIN COMPOSITIONS FOR TREATING INSULIN RESISTANCE

(75) Inventors: Ezio Ghigo, Turin (IT); Aart Jan Van Der Lely, Bergschenhoek (NL)

(73) Assignee: Alizé Pharma SAS, Ste-Foy-les-Lyons (FR)

( * ) Notice: Subject to any disclaimer, the term of this patent is extended or adjusted under 35 U.S.C. 154(b) by 151 days.

(21) Appl. No.: 10/595,485

(22) PCT Filed: Oct. 22, 2004

(86) PCT No.: PCT/CA2004/001858

§ 371 (c)(1),
(2), (4) Date: Sep. 6, 2007

(87) PCT Pub. No.: WO2005/039624

PCT Pub. Date: May 6, 2005

(65) Prior Publication Data

US 2008/0261872 A1    Oct. 23, 2008

(51) Int. Cl.
*A61K 38/00* (2006.01)
(52) U.S. Cl. .......................... 514/12; 530/300; 530/308
(58) Field of Classification Search .................. None
See application file for complete search history.

(56) References Cited

U.S. PATENT DOCUMENTS

| 4,554,101 A | 11/1985 | Hopp |
| 7,485,620 B2 | 2/2009 | Ghigo et al. |

FOREIGN PATENT DOCUMENTS

| CA | 2470235 | 6/2003 |
| CA | 2471879 | 11/2003 |
| WO | WO-01/56592 | 8/2001 |
| WO | 01/87335 | 11/2001 |
| WO | WO-01/92292 | 12/2001 |
| WO | WO-02/060472 | 8/2002 |
| WO | 03/051389 | 6/2003 |

OTHER PUBLICATIONS

Ariyasu, H. et al., "Stomach is a Major Source of Circulating Ghrelin, and Feeding State Determines Plasma Ghrelin-Like Immunoreactivity Levels in Humans", The Journal of Clinical Endocrinology & Metabolism, vol. 86, No. 10 (2001) pp. 4753-4758.
Bednarek, M. A. et al., "Structure—Function Studies on the New Growth Hormone-Releasing Peptide Ghrelin: Minimal Sequence of Ghrelin Necessary for Activation of Growth Hormone Secretagogue Receptor 1a", J. Med. Chem, vol. 43 (2000) pp. 4370-4376.
Caixas, A. et al., "Insulin, unlike Food Intake, does not Suppress Ghrelin in Human Subjects", The Journal of Clinical Endocrinology & Metabolism, vol. 87, No. 4 (2002) pp. 1902-1906.
Chapman, I. et al. "Enhancement of Pulsatile Growth Hormone Secretion by Continuous Infusion of a Growth Hormone-Releasing Peptide Mimetic, L-692,429, in Older Adults—A Clinical Research Center Study." Journal of Clinical Endocrinology and Metabolism, vol. 81, No. 8 (1996) pp. 2874-2880.
Chapman, I. et al., "Oral Administration of Growth Hormone (GH) Releasing Peptide-Mimetic MK-677 Stimulates the GH/Insulin-Like Growth Factor-I Axis in Selected GH-Deficient Adults", Journal of Clinical Endocrinology and Metabolism, vol. 82, No. 10 (1997) pp. 3455-3463.
Cummings, D. E. et al., "A Preprandial Rise in Plasma Ghrelin Levels Suggests a Role in Meal Initiation in Humans", Diabetes, vol. 50 (Aug. 2001) pp. 1714-1719.
Date, Y. et a., "Ghrelin Acts in the Central Nervous System to Stimulate Gastric Acid Secretion", Biochemical and Biophysical Research Communications, vol. 280 (2001) pp. 904-907.
Date, Y. et al., "Ghrelin is Present in Pancreatic α-Cells of Humans and Rats and Stimulates Insulin Secretion", Diabetes, vol. 51 (Jan. 2002) pp. 124-129.
Date, Y. et al., "Ghrelin, a Novel Growth Hormone-Released Acylated Peptide, Is Synthesized in a Distinct Endocrine Cell Type in the Gastrointestinal Tracts of Rats and Humans." Endocrinology, vol. 141, No. 11 (2000) pp. 4255-4261.
European Office Action, corresponding to European Application No. 02787266.2, Oct. 7, 2008.
Furuse, M. et al., "Intracerebroventricular injection of ghrelin and growth hormone releasing factor inhibits food intake in neonatal chicks", Neuroscience Letters, Vo. 301 (2001) pp. 123-126.
Gualillo et al. "Ghrelin, A Novel Placental-Derived Hormone", Endocrinology, vol. 142, No. 2, (2001) pp. 788-794.
Hattori et al. "GH, GH Receptor, GH Secretagogue Receptor, and Ghrelin Expression in Human T Cells, B Cells, and Neutrophils." The Journal of Clinical Endocrinology and Metabolism, vol. 86, No. 9 (2001) pp. 4284-4291.
Horvath, T. L. et al., "Minireview: Ghrelin and the Regulation of Energy Balance—A hypothalamic Perspective", Endocrinology, vol. 142, No. 10 (2001) pp. 4163-4169.
Inui, Akio, "Ghrelin: An orexigenic and Somatotrophic Signal from the Stomach", Nature Reviews, vol. 2 (Aug. 2001) pp. 1-10.
Kamegai, J. et al., "Central Effect of Ghrelin, an Endogenous Growth Hormone Secretagogue, on Hypothalamic Peptide Gene Expression", Endocrinology, vol. 141, No. 12, 2000, pp. 4797-4800.
Kamegai, J. et al., "Chronic Central Infusion of Ghrelin Increases Hypothalamic Neuropeptide Y and Agouti-Related Protein mRNA Levels and Body Weight in Rats", Diabetes, vol. 40 (Nov. 2001) pp. 2438-2443.

(Continued)

Primary Examiner—Robert Landsman
Assistant Examiner—Gyan Chandra
(74) Attorney, Agent, or Firm—Wilmer Cutler Pickering Hale and Dorr LLP

(57) ABSTRACT

A novel combination of ghrelin and unacylated ghrelin is described herein. Methods of administering and uses of this combination to alter an insulin-associated parameter are also described. Compositions and packages containing ghrelin and/or one of its analogs and nonacylated ghrelin and/or one of its analogs as well as the uses of such compositions in providing therapeutic benefit to human patients diagnosed with for example insulin resistance, diabetes and obesity are described.

28 Claims, 17 Drawing Sheets

OTHER PUBLICATIONS

Kojima et al. "Ghrelin is a growth-hormone-releasing acylated peptide from stomach" *Nature*, vol. 402, Dec. 9, 1999. (pp. 656-660).

Korbonits et al. "The presence of ghrelin in normal and adenomatous human pituitary," Department of Endocrinology, St. Bartholomew's Hospital, London, UK and Department of Biochemistry, National Cardiovascular Center Institute, Fujishirodau, Suita, Osaka Japan (11 pgs), 2009.

Lucid!, P. et al., "Ghrelin is not Necessary for Adequate Hormonal Counterregulation of Insulin-Induced Hypoglycemia", Diabetes, vol. 51 (Oct. 2002) pp. 2911-2914.

Masuda, Y. et al., "Ghrelin Stimulates Gastric Acid Secretion and Motility in Rats", Biochemical and Biophysical Research Communications, vol. 276 (2000) pp. 905-908.

Matsumoto, M. et al., "Structure-Activity Relationship of Ghrelin: Pharmacological Study of Ghrelin Peptides", Biochemical and Biophysical Research Communications, vol. 287 (2001), pp. 142-146.

Mori, K. et al., "Kidney produces a novel acylated peptide, ghrelin", FEBS Letters, vol. 486 (2000) pp. 213-216.

Muccioli, G. et al. "Neuroendocrine and peripheral activities of ghrelin: implications in metabolism and obesity," European Journal of Pharmacology, vol. 440 (2002) pp. 235-254.

Muccioli, G. et al., "Binding of 125I-labeled ghrelin to membranes from human hypothalamus and pituitary gland", J. Endocrinol. Invest., vol. 24 (2001) pp. RC7-RC9.

Muller, A. F. et al., "Blockade of the Growth Hormone (GH) Receptor Unmasks Rapid GH-Releasing Peptide-6-Mediated Tissue-Specific Insulin Resistance", The Journal of Clinical Endocrinology & Metabolism, vol. 86, No. 2, 2001, pp. 590-593.

Nagaya, N. et al., "Hemodynamic and hormonal effects of human ghrelin in healthy volunteers", Am J. Physiol Regulatory Integrative Comp. Physiol., vol. 280 (2001) pp. R1483-R1487.

Nakagawa, E. et al., "Hyperglycaemia suppresses the secretion of ghrelin, a novel growth-hormone-releasing peptide: responses to the intravenous and oral administration of glucose", Clinical Science, vol. 103 (2002) pp. 325-328.

Okumura, H. et al., "Vasodilatory Effect of Ghrelin, an Endogenous Peptide from the Stomach", Journal of Cadiovascular Pharmacology, vol. 39 (2002) pp. 779-783.

Pagotto, U. et al., "Plasma Ghrelin, Obesity, and the Polycystic Ovary Syndrome: Correlation with Insulin Resistance and Androgen Levels", The Journal of Clinical Endocrinology & Metabolism, vol. 87, No. 12 (2002) pp. 5625-5629.

Saad, M. et al., "Insulin Regulates Plasma Ghrelin Concentration", The Journal of Clinical Endocrinology & Metabolism, vol. 87, No. 8 (2002) pp. 3997-4000.

Svensson, J. et al., "Two-Month Treatment of Obese Subjects with the Oral Growth Hormone (GH) Secretagogue MK-677 Increases GH Secretion, Fat-Free Mass, and Energy Expenditure", Journal of Clinical Endocrinology and Metabolism. vol. 83, No. 2 (1998) pp. 362-369.

Tanka, M. et al., "Testis-specific and developmentally induced expression of a ghrelin gene-deprived transcript that encodes a novel polypeptide in the mouse", Biochimica et Biophysica Acta, vol. 1522 (2001) pp. 62-65.

Tena-Sempere, M. et al., "Novel Expression and Functional Role of Ghrelin in Rat Testis", Endocrinology, vol. 143, No. 2, 2002, pp. 717-725.

Tolle, V. et al., "Ultradian Rhythmicity of Ghrelin Secretion in Relation with GH, Feeding Behavior, and Sleep-Wake Patterns in Rats", Endocrinology, vol. 143, No. 4 (2002) pp. 1353-1361.

Tschop, M. et al., "Ghrelin induces adiposity in rodents", Letters to Nature, vol. 407 (Oct. 19, 2000) pp. 908-913.

Volante, et al. "Extensive DNA Fragmentation in Oxyphilic Cell Lesions of the Thyroid," The Journal of Histochemistry and Cytochemistry, vol. 49, No. 8 (2001) pp. 1003-1011.

Volante, M. et al., "Expression of Ghrelin and of the GH Secretagogue Receptor by Pancreatic Islet Cells and Related Endocrine Tumors", The Journal of Clinical Endocrinology & Metabolism, vol. 87, No. 3 (2002) pp. 1300-1308.

Volante, M. et al., "Ghrelin Expression in Fetal, Infant, and Adult Human Lung", The Journal of Histochemistry & Cytochemistry, vol. 50, No. 8 (2002) pp. 1013-1021.

Wierup, N. et al., "The ghrelin cell: a novel developmentally regulated islet cell in the human pancreas", Regulatory Peptides, vol. 107 (2002) pp. 63-69.

Wren, A. M. et al., "Ghrelin Enhances Appetite and Increases Food Intake in Humans", The Journal of Clinical Endocrinology & Metabolism, vol. 86, No. 12 (2001) pp. 5992-5995.

Wren, A.M. et al., "The Novel Hypothalamic Peptide Ghrelin Stimulates Food Intake and Growth Hormone Secretion", Endocrinology, vol. 141, No. 11 (2000) pp. 4325-4328.

Yoshihara, F. et al., "Ghrelin: a novel peptide for growth hormone release and feeding regulation", Genes and Nutrition, pp. 391-395.

Zhang, W. et al., "Inhibition of pancreatic protein secretion by ghrelin in the rat", Journal of Physiology, vol. 537, No. 1 (2001) pp. 231-236.

Mucciolo et al. "Neuroendocrine and peripheral activities of ghrelin: implications in metabolism and obesity," *European Journal of Pharmacology* 440 (2002) 235-254.

Office Action mailed on Mar. 20, 2009 in connection with U.S. Appl. No. 11/756,456, 12 pages.

Atkinson, Mark A. et al., "Type 1 diabetes: new perspectives on disease pathogenesis and treatment", The Lancet, vol. 358, Jul. 21, 2001, pp. 221-229.

Florez, Jose C., "The Genetics of Type 2 Diabetes: A Realistic Appraisal in 2008", J. Clin. Endocrinol Metab., 93 (12), pp. 4633-4642, Dec. 2008.

Adelhorst et al., J. Biol. Chem. 269: 6275-6278, 1994.

Broglio et al., "Non Acylated Gherlin Counteracts the Metabolic but not the Neuroendocrine REsponse to Acylated Ghrelin in Humans", Jorunal of Clinical Endocrinaology Metabolism, 89(6):3062-3065 (2004).

Cassoni et al., "Identification, Characterization and Biological Activity of Specific Receptors for Natural (Ghrelin) and Synthetic Growth Hormone Secretagogues and Analogs in Human Breast Carcinomas and Cell Lines", Journal of Clinical Endocrinology and Metabolism, 83(4):1738-1745 (2001).

Granata, Riccarda et al. "Acylated and unacylated ghrelin promote proliferation and inhibit apoptosis of pancreatic beta cells and human inslets: involvement of 3', 5'- cyclic adenosine monphophate/protein kinase A, extracellular signal-regulated kinase 1/2, and phosphatidyl inositol 3-kinase/Akt signaling." Endocrinology, Feb. 2007, 148(2), pp. 512-529.

Granata, Riccarda et al. "Acylated and unacylated ghrelin promote proliferation and inhibit serum stravation- and cytokine-induced apoptosis of pancreatic beta cells through cAMP/PKA, ERK1/2 and P13K/Akt.", abstract and poster presented at "Endocrine Society Meeting," Boston, from Jun. 24, 2006-Jun. 27, 2006.

International Search Report, PCT/CA2002/001964.

International Search Report, PCT/CA2004/001858.

Marzullo et al., J. Clin. Endocr. Metab. 89: 936-939, 2004.

Mickle et al., Medical Clin. North Am., 2000, vol. 84(3), p. 597-607.

Poykko, et al., "Low Plasma Ghrelin is Associated with Insulin REsistance, Hypertension and the Prevalence of Type 2 Diabetes", Diabetes, 52:2546-2553 (2003).

Prodam, Flavia et al. "Unacylated ghrelin (UAG) enhances the early insulin response to meal, improves glucose metabolism and decrease free fatty acids levels in healthy volunteers." Abstract and poster presented at "European Congress of Endocrinology," Budapest, from Apr. 28, 2007-May 2, 2007.

Toshinai, et al., "Upregulation of Ghrelin Expresion in the Stomach upon Fastin, Insulin-Induced Hypoglycemia and Leptin Administration", Biochemical and Biophysical Research Communications, 281(5):1220-1225 (2001).

Broglio, F. et al., "Ghrelin, A Natural GH Secretagogue Produced by the Stomach, Induces Hyperglycemia and Reduces Insulin Secretion in Humans," J. Clin. Endocrinol. & Metab., 86(10): 5083-5086 (2001).

Van Der Lely, A. et al., "Biological, Physiological, Pathophysiological, and Pharmacological Aspects of Ghrelin", *Endocrine Reviews*, 25(3): pp. 426-457 (2004).

SEQUENCE LISTING

<160> NUMBER OF SEQ ID NOS: 4

<210> SEQ ID NO 1
<211> LENGTH: 28
<212> TYPE: PRT
<213> ORGANISM: Homo sapiens
<220> FEATURE:
<221> NAME/KEY: MOD_RES
<222> LOCATION: (3)
<223> OTHER INFORMATION: octanoyl-Ser

<400> SEQUENCE: 1

Gly Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 2
<211> LENGTH: 28
<212> TYPE: PRT
<213> ORGANISM: Homo sapiens

<400> SEQUENCE: 2

Gly Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 3
<211> LENGTH: 27
<212> TYPE: PRT
<213> ORGANISM: Homo sapiens
<220> FEATURE:
<221> NAME/KEY: MOD_RES
<222> LOCATION: (3)
<223> OTHER INFORMATION: octanoyl-Ser

<400> SEQUENCE: 3

Gly Ser Ser Phe Leu Ser Pro Glu His Gln Arg Val Gln Arg Lys Glu
 1               5                  10                  15

Ser Lys Lys Pro Pro Ala Lys Leu Gln Pro Arg
            20                  25

<210> SEQ ID NO 4
<211> LENGTH: 27
<212> TYPE: PRT
<213> ORGANISM: Homo sapiens

<400> SEQUENCE: 4

Gly Ser Ser Phe Leu Ser Pro Glu His Gln Arg Val Gln Arg Lys Glu
 1               5                  10                  15

Ser Lys Lys Pro Pro Ala Lys Leu Gln Pro Arg
            20                  25

USE OF GHRELIN AND UNACYLATED GHRELIN COMPOSITIONS FOR TREATING INSULIN RESISTANCE

FIELD OF THE INVENTION

The invention relates to modulation of hormone-related processes and in particular to the modulation of insulin-related processes.

BACKGROUND OF THE INVENTION

Insulin tightly regulates glucose uptake and metabolism, and therefore modulation of insulin activity and in turn glucose levels in the blood can have significant physiological effects. Many pathologies are either caused or enhanced by variations in insulin levels and the onset of insulin tolerance or resistance (i.e. a state where cells become less responsive or unresponsive to the insulin signal).

In type I diabetes (diabetes mellitus), the pancreatic production of insulin is greatly reduced. Hence type I diabetics need regular injections or perfusions of insulin to control their blood glucose to avoid deleterious consequences. Some type I diabetics also develop the "dawn syndrome", a state of increased insulin resistance in the early hours of the morning.

In type II diabetes (non-insulin dependent diabetes or NIDD), individuals, usually overweight, develop an insulin resistance and hyperinsulinemia (high levels of insulin). Although some drugs may restore insulin sensitivity to a certain extent, type II diabetics usually have to change their lifestyle and lose weight to maintain control of their blood glucose level.

Individuals that have higher levels of growth hormone (GH), namely people affected with acromegaly or certain pituitary tumors, tend to develop insulin resistance. High blood levels of free fatty acids (FFA) and GH itself are thought to play an important role in the onset and maintenance of insulin resistance in these individuals.

Individuals that having lower than normal levels of GH, i.e. a GH deficiency, also tend to develop insulin resistance. GH deficiency favours fat mass gain and, therefore, insulin resistance. In addition, GH replacement therapy may exacerbate insulin resistance in these subjects through the production of free fatty acids.

Obesity also causes insulin resistance and, ultimately, NIDD. It has been shown that obese individuals have a lower than normal levels of GH. These results strongly suggest that the regulation and control of insulin, GH and body weight are all interrelated.

Insulin resistance may also increase under postprandial conditions (i.e. following feeding).

It would thus be desirable to have new strategies of therapeutic intervention relating to such processes.

SUMMARY OF THE INVENTION

The invention relates to a modulation of insulin-related processes and uses thereof.

In a first aspect, the invention provides a method of altering an insulin-associated parameter in a subject, said method comprising administering to said subject a ghrelin or analog thereof; and an unacylated ghrelin or analog thereof.

In an embodiment, the method comprises administering to said subject a composition comprising a ghrelin or analog thereof; and an unacylated ghrelin or analog thereof. In an embodiment, the composition further comprises a pharmaceutically acceptable carrier.

In a further aspect, the invention provides a composition comprising a ghrelin or analog thereof and an unacylated ghrelin or analog thereof. In an embodiment, the composition further comprises a pharmaceutically acceptable carrier.

In a further aspect, the invention provides a kit or package (e.g. a commercial package) comprising a ghrelin or analog thereof and an unacylated ghrelin or analog thereof or the above-mentioned composition.

In an embodiment, the kit or package further comprises instructions for altering an insulin-associated parameter in a subject.

The invention further provides a use of the above-mentioned composition for the alteration of an insulin-associated parameter in a subject.

The invention further provides a use of the above-mentioned composition for the preparation of a medicament for the alteration of an insulin-associated parameter in a subject.

The invention further provides a composition comprising a ghrelin or analog thereof and an unacylated ghrelin or analog thereof for use as a medicament.

The invention further provides a use of a composition comprising a ghrelin or analog thereof and an unacylated ghrelin or analog thereof as a medicament.

In an embodiment, the insulin-associated parameter is selected from the group consisting of: (a) insulin level; (b) insulin resistance; (c) free fatty acid level; (d) insulin activity; (e) insulin sensitivity; and (f) any combination of (a) to (e).

In an embodiment, the alteration of an insulin-associated parameter is selected from the group consisting of: (a) a decrease in insulin level; (b) a decrease in insulin resistance; (c) a decrease in free fatty acid level; and (d) any combination of (a) to (c).

In an embodiment, the method is for preventing or treating an insulin-associated condition.

In an embodiment, the insulin-associated parameter is insulin resistance.

In an embodiment, the insulin resistance is associated with a state or condition selected from the group consisting of: (a) postprandial state; (b) reduced growth hormone level; (c) reduced growth hormone activity; (d) obesity; (e) diabetes; (f) intravenous nutrition due to critical illness; (g) metabolic syndrome X; and (h) any combination of (a) to (g).

In an embodiment, the condition is reduced growth hormone level, activity, or both.

In an embodiment, the growth hormone level, activity, or both are associated with a condition selected from the group consisting of: (a) obesity; (b) aging; (c) pituitary gland deficiency; (d) intravenous nutrition; and (e) any combination of (a) to (d).

In an embodiment, the condition is diabetes.

In an embodiment, the diabetes is selected from the group consisting of type I diabetes and type II diabetes.

In an embodiment, the diabetes is type I diabetes.

In an embodiment, the method, use or composition noted above is for preventing or treating the dawn phenomenon.

In an embodiment, the administration of said ghrelin or analog thereof and said unacetylated ghrelin or analog thereof is sequential, in a further embodiment, simultaneous.

In an embodiment, the ghrelin comprises an amino acid sequence substantially identical to a sequence selected from the group consisting of SEQ ID NO: 1 and a fragment thereof. In an embodiment, the ghrelin comprises a peptide having the amino acid sequence of SEQ ID NO: 1.

In an embodiment, the unacylated ghrelin comprises an amino acid sequence substantially identical to a sequence selected from the group consisting of SEQ ID NO: 2 and a fragment thereof. In an embodiment, the unacylated ghrelin comprises a peptide having the amino acid sequence of SEQ ID NO: 2.

In an embodiment, the analog of ghrelin comprises an amino acid sequence substantially identical to a sequence selected from the group consisting of SEQ ID NO: 3 and a fragment thereof. In an embodiment, the analog of ghrelin comprises a peptide having the amino acid sequence of SEQ ID NO: 3.

In an embodiment, the analog of unacylated ghrelin comprises an amino acid sequence substantially identical to a sequence selected from the group consisting of SEQ ID NO: 4 and a fragment thereof. In an embodiment, the analog of unacylated ghrelin comprises a peptide having the amino acid sequence of SEQ ID NO: 4.

In an embodiment, the ghrelin or analog thereof and said unacylated ghrelin or analog thereof and/or the above-mentioned composition is administered (e.g. the composition is adapted for administration) through a route selected from the group consisting of intravenous, oral, transdermal, subcutaneous, mucosal, intramuscular, intranasal, intrapulmonary, parenteral, intrarectal and topical.

In an embodiment, the ghrelin or analog thereof is administered at a dose of about 1 µg/kg.

In an embodiment, the unacetylated ghrelin or analog thereof is administered at a dose of about 1 µg/kg.

In an embodiment, the subject is a mammal, in a further embodiment, a human.

In an embodiment, the above-noted subject suffers from a GH deficiency and/or is in a GH-deficient state.

BRIEF DESCRIPTION OF THE DRAWINGS

The following abbreviations are used herein.

AG=ghrelin or acylated ghrelin; UAG=unacylated ghrelin; GH=growth hormone

DETAILED DESCRIPTION OF THE INVENTION

Figure 1:
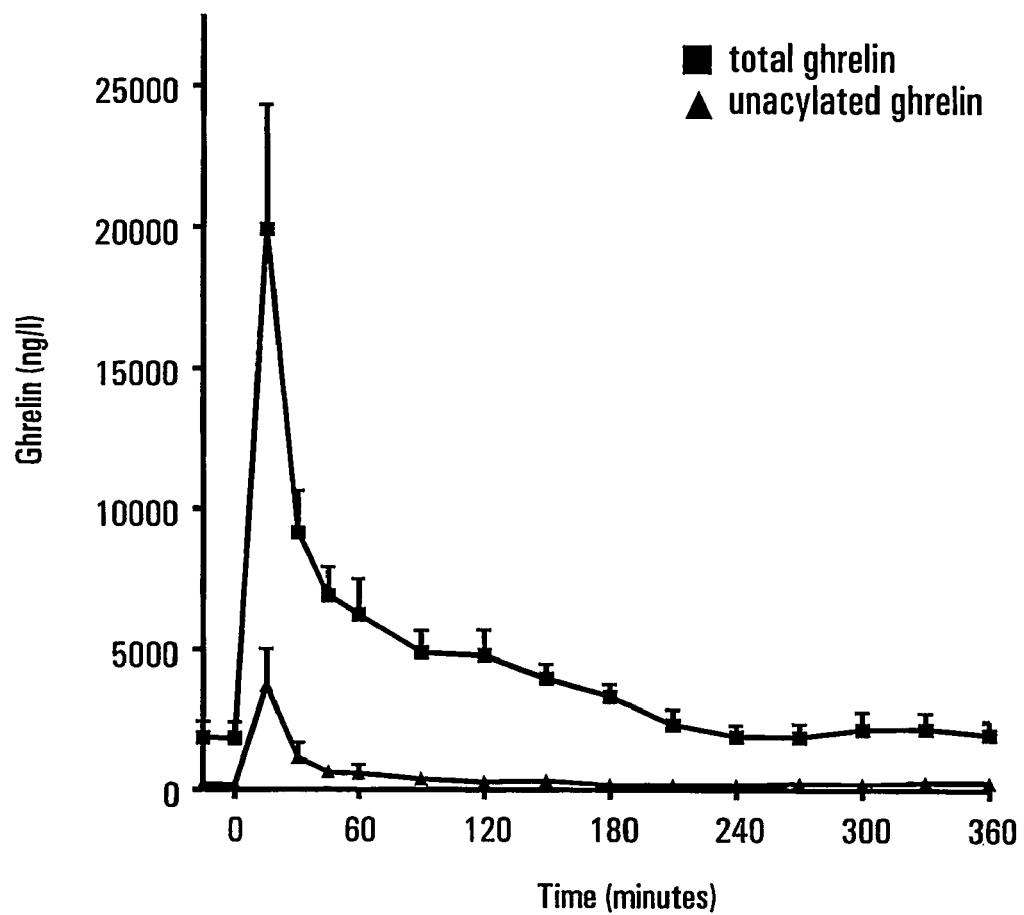
FIG. 1: Total (■) and acylated (▲) ghrelin concentrations (ng/l) after an i.v. bolus injection of 1 µg/kg acylated ghrelin in 6 GH deficient subjects after an overnight fast.
Figure 2A:
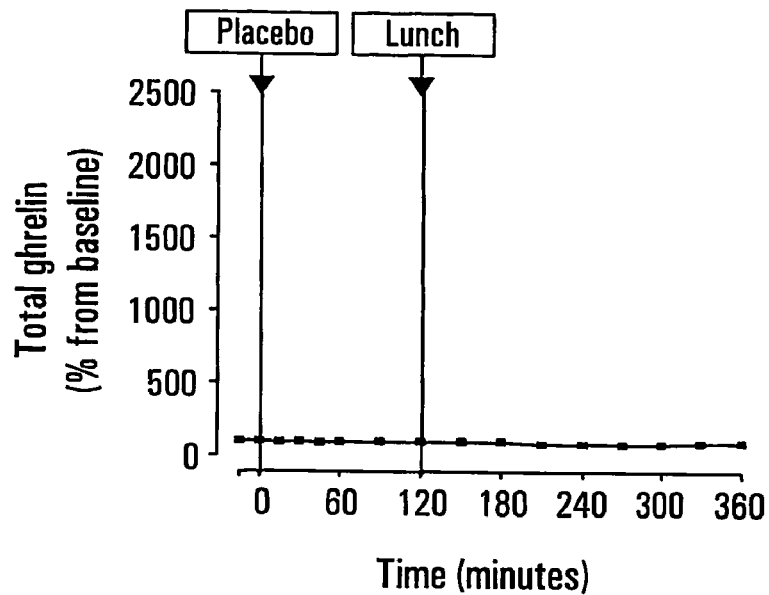
FIGS. 2A-2E: Changes in serum total ghrelin concentrations as % of baseline in 6 GH deficient subjects after administration of (A) placebo, (B) AG and GH, (C) AG only, (D) UAG only and (E) AG and UAG. AG=acylated ghrelin (1 µg/kg intravenous or i.v.); UAG=unacylated ghrelin (1 µg/kg i.v.); GH=growth hormone (normal daily replacement dose).
Figure 2B:
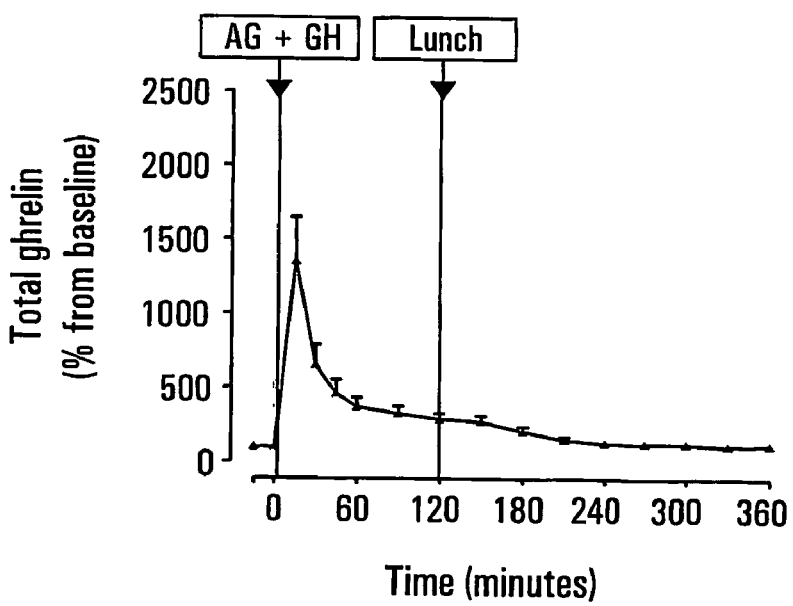
Figure 2C:
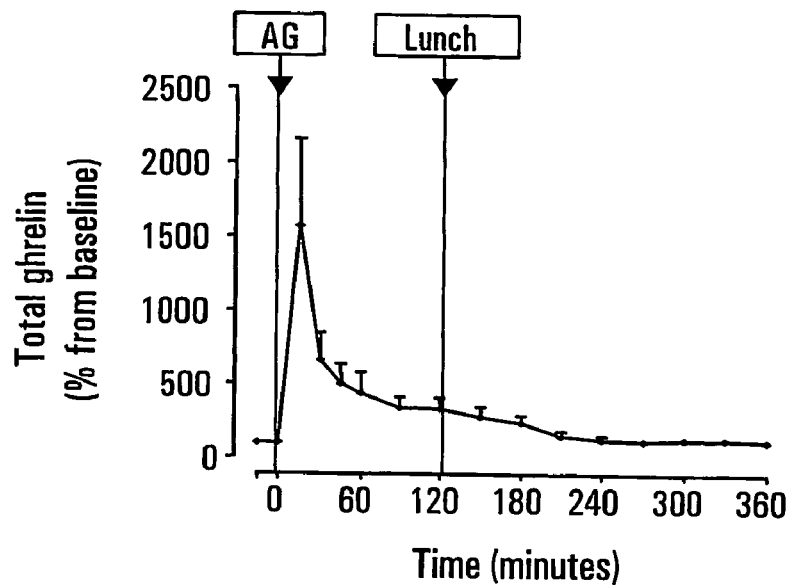
Figure 2D:
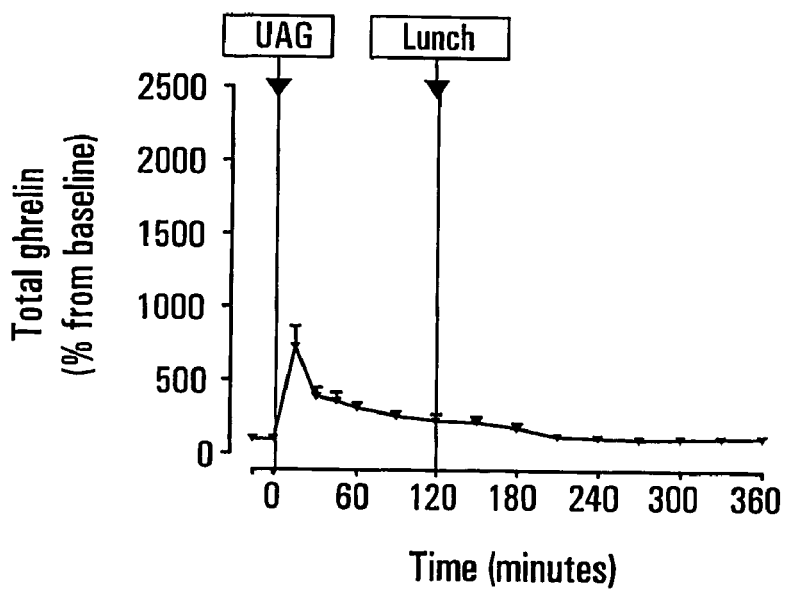
Figure 2E:
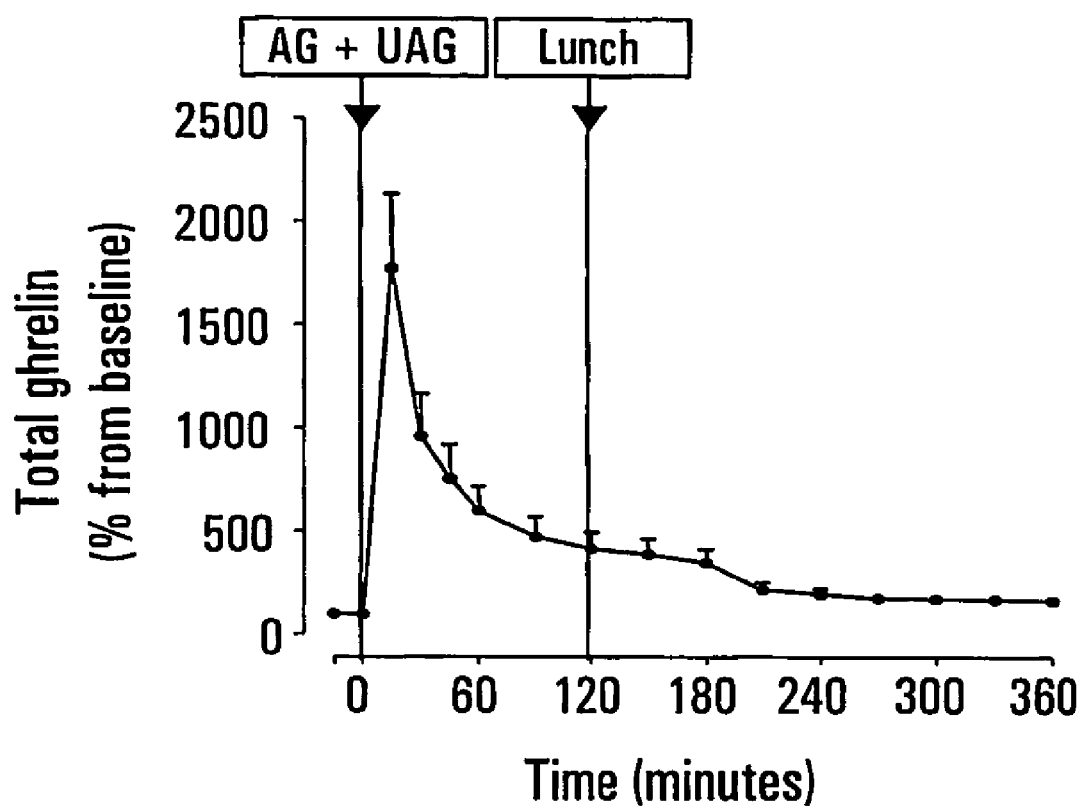
Figure 3A:
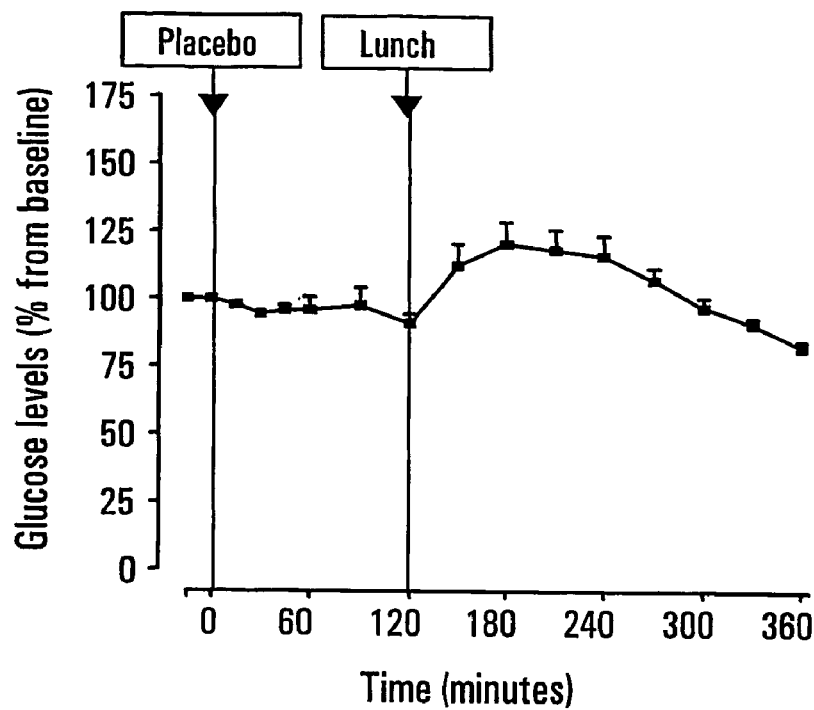
FIGS. 3A-3E: Changes in serum glucose concentrations as % of baseline in 6 GH deficient subjects after administration of (A) placebo, (B) AG and GH, (C) AG only, (D) UAG only and (E) AG and UAG. AG=acylated ghrelin (1 µg/kg i.v.); UAG=unacylated ghrelin (1 µg/kg i.v.); GH=growth hormone (normal daily replacement dose).
Figure 3B:
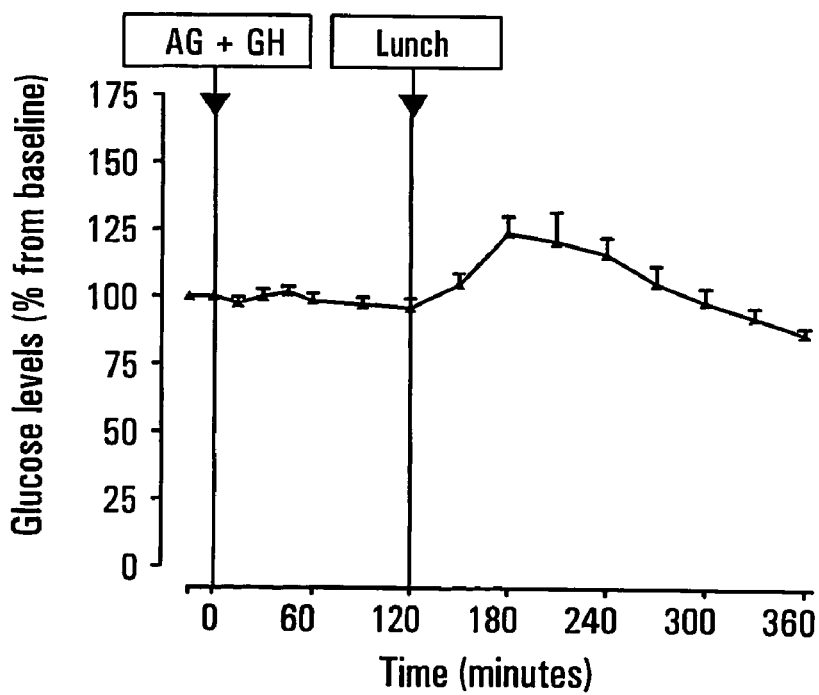
Figure 3C:
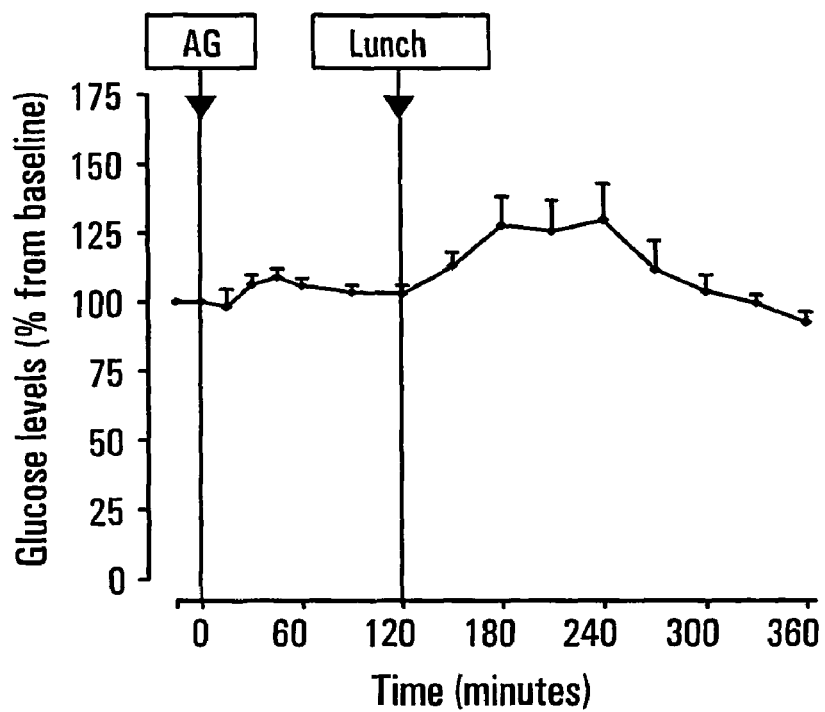
Figure 3D:
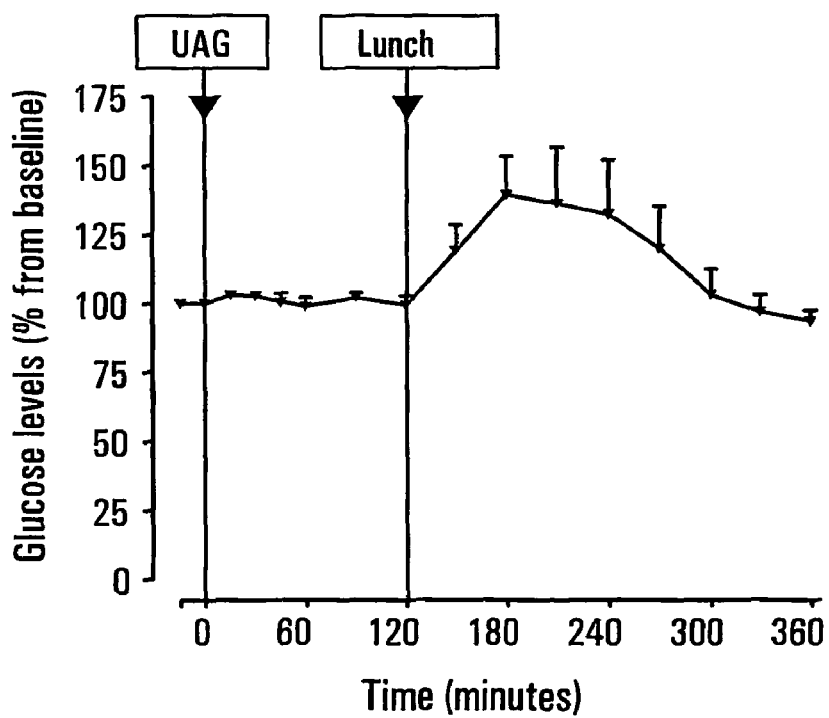
Figure 3E:
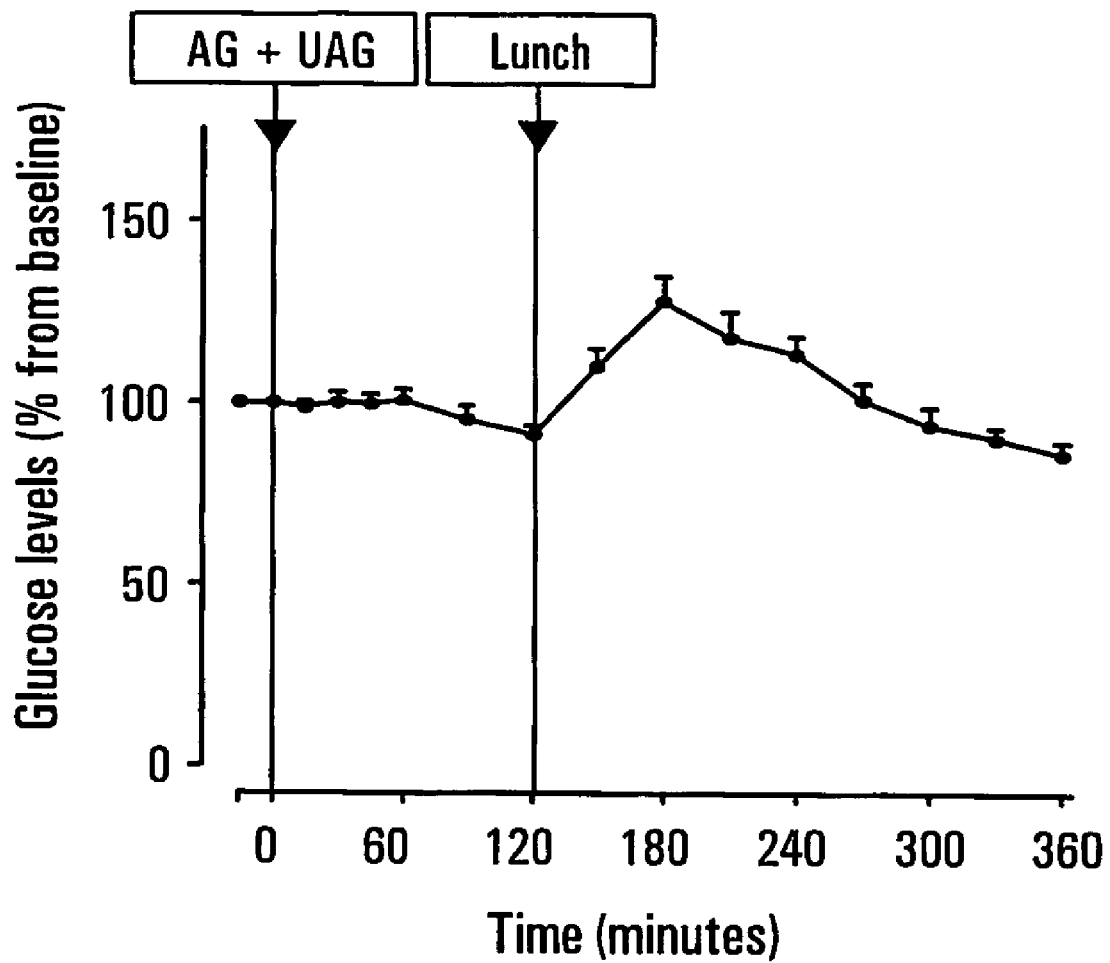

The invention relates to the use of ghrelin (also referred to as "acylated ghrelin") and unacylated ghrelin to modulate processes related to insulin levels and/or activity.

Ghrelin is a 28 amino acid hormone which is predominantly produced by the stomach, but it is also detectable in many other tissues as well (1-12). Ghrelin can stimulate growth hormone (GH) secretion, which is mediated by the activation of GH secretagogue type 1a (GHS1a) receptor. However, ghrelin exhibits additional activities including e.g. stimulation of prolactin and ACTH secretion, stimulation of a positive energy balance, gastric motility and acid secretion, but also modulation of pancreatic exocrine and endocrine function as well as effects on glucose levels (2, 9, 13-28). Ghrelin is the first natural hormone in which the hydroxyl group of one of its serine residues is acylated by n-octanoic acid (1). This acylation is essential for binding to the GHS1a receptor and for the GH-releasing capacity of ghrelin (1, 29-31). Ghrelin has been reported to be expressed by pancreatic endocrine α-cells, in rat and human tissues, by some authors (32) and by pancreatic β-cells according to others (33). Moreover, ghrelin is not known to be co-expressed with any known islet hormone (34). Ghrelin appears to exert a tonic inhibitory regulation on insulin secretion from pancreatic β-cells, and a negative association between ghrelin and insulin secretion has been found in humans as well as in other animals by some (23, 35-39), although not by others (40). Also, ghrelin induces a significant increase in human plasma glucose levels which is surprisingly followed by a reduction in insulin secretion (17). It has been reported that acute, as well as chronic treatment with GHS (GH secretagogues), particularly non-peptidyl derivatives, induces hyperglycemia and insulin resistance in a considerable number of elderly subjects and obese patients (41-43). This suggests that ghrelin exerts a significant role in the fine-tuning of insulin secretion and glucose metabolism. Also, ghrelin secretion may be suppressed, at least in part, by an increased plasma glucose level as well as by insulin as shown by hyperinsulinemic euglycemic clamp studies in healthy subjects (38, 44, 45). It has also been suggested that ghrelin could have direct stimulatory effects on glycogenolysis (17).

PCT international application WO 01/87335A2 (published Nov. 22, 2001) discloses methods of selectively inhibiting ghrelin action including those on obesity using growth hormone secretagogue receptor antagonists and ghrelin neutralizing reagents. The ghrelin neutralizing reagents are antibodies, single chain antibodies, antibody fragments, or antibody-based constructs.

Unacylated ghrelin (i.e. lacking the above-noted octanoyl modification) is not a ligand for the growth hormone secretagogue receptor and is not known to bind ghrelin for neutralizing purposes.

PCT application WO 03/051389 (published Jun. 26, 2003) relates to unacylated ghrelin and uses thereof.

In the results described herein, the effects of ghrelin on glucose and insulin kinetics in humans were investigated. In this regard, the effects of a single intravenous administration of placebo, acylated ghrelin (AG), unacylated ghrelin (UAG) and a combination of AG and UAG after an overnight fast in adult-onset GH-deficient patients, on glucose and free fatty acid (FFA) metabolism were studied, before and after a standard lunch, and with or without the presence of GH. For these studies, the human forms of AG, UAG and GH were used. Such studies were pursued to determine the acute effects of human ghrelin on parameters of glucose and lipid metabolism with or without the presence of GH and to determine whether UAG has any intrinsic effects, but also whether UAG can modify the effects of AG.

As shown herein, a combination of ghrelin and unacylated ghrelin inhibited peripheral actions of acylated ghrelin on a parameter of metabolism chosen from insulin, glucose and free fatty acids. To provide therapeutic benefits to subjects in various states of insulin resistance, in an embodiment those associated with low GH action and/or increased acylated ghrelin secretion, a combination of ghrelin (in an embodiment, NH$_2$-Gly-Ser-[octanoyl]Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg [SEQ ID NO: 1]) or an analog thereof analog and unacylated ghrelin (in an embodiment, NH$_2$-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg [SEQ ID NO: 2]) or an analog thereof, may be administered to a subject. In embodiments, such administration may be intravenous, subcutaneous, transdermal, oral or by inhalation. In embodiments, a suitable pharmaceutical composition is administered. Preparation of such pharmaceutical compositions suitable for intravenous, subcutaneous, transdermal, oral, buccal, sublingual and pulmonary delivery are known in the art.

"Ghrelin" and "acylated ghrelin" are used interchangeably herein. Ghrelin as used herein refers to the 28 amino acid sequence set forth in SEQ ID NO: 1 below, having an octanoyl modification of Ser at the third position of the peptide.

Gly-Ser-[octanoyl]Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO: 1)

"Unacylated ghrelin" comprises a peptide that lacks the octanoyl modification at Ser-3 noted above. In an embodiment, unacylated ghrelin comprises the peptide set forth in SEQ ID NO: 2 below.

Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg (SEQ ID NO: 2)

Naturally-occurring variations of unacylated ghrelin include peptides that contain substitutions, additions or deletions of one or more amino acids, which in embodiments may result from changes in the nucleotide sequence of the encoding ghrelin gene or its alleles thereof or due to alternative splicing of the transcribed RNA. It is understood that such changes do not substantially affect the antagonistic properties, nor the pharmacological and biological characteristics of unacylated ghrelin variant. The peptides may be in the form of salts; in embodiments the acidic functions of the molecule may be replaced by a salt derivative thereof, such as a trifluoroacetate salt.

"Analog of ghrelin" refers to both structural and functional analogs of ghrelin which are capable of replacing ghrelin. Simple structural analogs comprise peptides substantially identical to or showing homology with unacylated ghrelin as set forth in SEQ ID NO: 1 or a fragment thereof. For example, an isoform of ghrelin or ghrelin-28 is des Gln-14 Ghrelin (a 27 amino acid peptide possessing serine 3 modification by n-octanoic acid) set forth in SEQ ID NO: 3 below.

Gly-Ser-[octanoyl]Ser-Phe-Leu-Ser-Pro-Glu-His-Gln-Arg-Val-Gln-Arg-Lys-Glu-Ser-Lys-Lys-Pro-Pro-Ala-Lys-Leu-Gln-Pro-Arg (SEQ ID NO: 3)

des Gln-14 ghrelin is shown to be present in the stomach; it is functionally identical to ghrelin in that it binds to GHS-R1a with similar binding affinity, elicits $Ca^{2+}$ fluxes in cloned cells and induces GH secretion with similar potency as Ghrelin-28. In an embodiment, des-Gln14-ghrelin is therefore a structural functional analog of ghrelin.

"Analog of unacylated ghrelin" refers to both structural and functional analogs of unacylated ghrelin which are capable of replacing unacylated ghrelin, e.g. in antagonizing the peripheral actions of ghrelin. Simple structural analogs comprise peptides substantially identical to or showing homology with unacylated ghrelin as set forth in SEQ ID NO: 2 or a fragment-thereof. In an embodiment, it is envisioned that unacylated des-gln14-ghrelin, which lacks the octanoyl group of Ser-3, could potentially antagonize effects of ghrelin and des-Gln14-ghrelin on peripheral metabolism involving insulin secretion and glycemic control. In an embodiment, unacylated des Gln-14 ghrelin comprises the peptide set forth in SEQ ID NO: 4 below.

Gly-Ser-Ser-Phe-Leu-Ser-Pro-Glu-His-Gln-Arg-Val-Gln-Arg-Lys-Glu-Ser-Lys-Lys-Pro-Pro-Ala-Lys-Leu-Gln-Pro-Arg (SEQ ID NO: 4)

Functional analogs of unacylated ghrelin may replace unacylated ghrelin in one or more biological activities exhibited by unacylated ghrelin. For example, these biological activities of unacylated ghrelin may include: binding to a specific receptor, altering the signals arising from the activation of a receptor, and modulating the functional consequences of activation of a receptor.

Functional analogs of unacylated ghrelin, as well as those of unacylated des-Gln14-ghrelin, may produce the biological effects of unacylated ghrelin in antagonizing the peripheral metabolic actions of ghrelin such as those on insulin levels and glycemic control, as described herein, hence such functional analogs are useful for therapeutic intervention in medical conditions, e.g. those involving GH-deficient states.

Conservative substitutions of one or more amino acids in the primary sequence of unacylated ghrelin may provide structural analogs of the peptide. In order to derive analogs of varied (e.g. greater) potency, various methods may be used such as alanine scans, selective substitutions with D-amino acid or synthetic amino acids, truncation of the peptide sequence in order to find a "functional core" of the peptide, covalent addition of molecules to improve the properties of the peptide such as its serum stability, in vivo half life, potency, hydrophilicity or hydrophobicity and immunogenicity.

Peptide compounds (or ligand or domain) of the invention can be prepared, for example, by replacing, deleting, or inserting an amino acid residue of a peptide compound described herein, with other conservative amino acid residues, i.e., residues having similar physical, biological, or chemical properties, and screening for biological function. It is well known in the art that some modifications and changes can be made in the structure of a polypeptide without substantially altering the biological function of that peptide, to obtain a biologically equivalent polypeptide. The peptides, ligands and domains of the present invention also extend to biologically equivalent peptides, ligands and domains that differ from a portion of the peptide sequences described herein by conservative amino acid substitutions. As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp. (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 1984). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently ($C_1$-$C_6$) alkyl, substituted ($C_1$-$C_6$) alkyl, ($C_1$-$C_6$) alkenyl, substituted ($C_1$-$C_6$) alkenyl, ($C_1$-$C_6$) alkynyl, substituted ($C_1$-$C_6$) alkynyl, ($C_5$-$C_{20}$) aryl, substituted ($C_5$-$C_{20}$) aryl, ($C_6$-$C_{26}$) alkaryl, substituted ($C_6$-$C_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine-3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

The above classifications are not absolute and an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatized moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. The exception with respect to the present invention is that unacylated ghrelin or analogs thereof are defined as lacking the octanoyl modification of the reside corresponding to Ser-3 noted above. Peptide analogs also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogs can also include replacement of the amide linkage in the peptide with a substituted amide (for example, groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl, or substituted ($C_1$-$C_6$) alkynyl) or isostere of an amide linkage (for example, —$CH_2$NH—, —$CH_2$S, —$CH_2$$CH_2$—, —CH=CH— (cis and trans), —C(O)$CH_2$—, —CH(OH)$CH_2$—, or —$CH_2$SO—).

Peptides or peptide analogs can be synthesised by standard chemical techniques, for example, by automated synthesis using solution or solid phase synthesis methodology. Automated peptide synthesisers are commercially available and use techniques well known in the art. General methods and synthetic strategies used in preparing peptides and in providing functional and structural analogs of peptides is described in publications such as "Solid phase peptide synthesis" by Stewart and Young, W. H. Freeman & Co., San Francisco, 1969 and Erickson and Merrifield, "The Proteins" Vol. 2, p. 255 et seq. (Ed. Neurath and Hill), Academic Press, New York, 1976.

In one aspect, the invention provides peptides/peptide compounds, that are purified, isolated or substantially pure, which in some embodiments are combined in a composition. A compound is "substantially pure" when it is separated from the components that naturally accompany it. Typically, a compound is substantially pure when it is at least 60%, more generally 75% or over 90%, by weight, of the total material in a sample. Thus, for example, a polypeptide that is chemically synthesised or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

"Homology" and "homologous" refer to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term "homologous" does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs 1-4.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In various embodiments, the peptides described herein may be used therapeutically in formulations or medicaments to prevent or treat conditions related to insulin levels and/or activity and related processes. The invention provides corresponding methods of medical treatment, in which a therapeutic dose of a such a peptide(s) is administered in a pharmacologically acceptable formulation, e.g. to a patient or subject in need thereof. Accordingly, the invention also provides therapeutic compositions comprising such (a) peptide(s), and a pharmacologically acceptable excipient or carrier. In one embodiment, such compositions include such (a) peptide(s) in a therapeutically or prophylactically effective amount sufficient to treat a condition related to insulin levels and/or activity. The therapeutic composition may be soluble in an aqueous solution at a physiologically acceptable pH.

A "therapeutically effective amount" refers to an amount effective, at dosages and for periods of time necessary, to achieve the desired therapeutic result, such as treatment of a condition related to insulin levels and/or activity. A therapeutically effective amount of the peptide(s) noted herein may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the onset of a condition related to insulin levels and/or activity. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound or compounds, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a peptide(s)/peptide compound(s) described herein can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. a peptide(s)/peptide compound(s) described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a peptide(s)/peptide compound(s) described herein may be formulated with one or more additional compounds that enhance its/their solubility.

In according with an aspect of the present invention, methods of altering an insulin-associated parameter in a subject are provided. In an embodiment, the methods comprise administering a ghrelin or analog thereof and an unacylated ghrelin or analog thereof. In another embodiment, the methods comprise administering a composition comprising a ghrelin or analog thereof, an unacylated ghrelin or analog thereof, and in a further embodiment, the composition also comprises a pharmaceutically acceptable carrier. As used herein, the term "insulin-associated parameter" is defined as a parameter that is associated with insulin levels and/or activity. Insulin is involved in many biological activities that include, but are not limited to, glucose metabolism and lipid metabolism (e.g. free fatty acid metabolism). In an embodiment, the insulin-associated parameter is selected from the group consisting of an insulin level, insulin resistance, free fatty acid level, insulin activity, insulin sensitivity and any combination thereof. In another embodiment, the alteration is an increase in the insulin-associated parameter (e.g. insulin activity or sensitivity). In yet another embodiment, the alteration is a decrease in the insulin-associated parameter (e.g. insulin level, insulin resistance, free fatty acid level). In embodiments, the insulin resistance may be associated with various states or conditions such as postprandial state, reduced growth hormone level and/or activity, or both, obesity, diabetes, intravenous nutrition due to critical illness, metabolic syndrome X or any combinations thereof. In embodiments, reduced growth hormone level and/or activity may be associated with various conditions such as obesity, aging, pituitary gland deficiency, intravenous nutrition or any combinations thereof. In embodiments, diabetes may be type I diabetes and/or type II diabetes, in a further embodiment, the method described herein is for preventing or treating the dawn phenomenon experienced by some type I diabetes subjects.

In accordance with another aspect of the invention, therapeutic compositions of the present invention, comprising a (a) peptide(s)/peptide compound(s) described herein, may be provided in containers or packages (e.g. commercial packages) which further comprise instructions for its/their use for the prevention and/or treatment of a condition related to insulin levels and/or activity.

Accordingly, the invention further provides a package comprising a peptide(s)/peptide compound(s) described herein or the above-mentioned composition together with instructions for its/their use for the prevention and/or treatment of a condition related to insulin levels and/or activity.

The invention further provides a use of a peptide(s)/peptide compound(s) described herein for the prevention and/or treatment of a condition related to insulin levels and/or activity.

The invention further provides a use of a peptide(s)/peptide compound(s) described herein for the preparation of a medicament for the prevention and/or treatment of a condition related to insulin levels and/or activity.

The invention thus relates to the combined use of (i) ghrelin and/or an analog thereof and (ii) unacylated ghrelin and/or an analog thereof. In embodiments, the use is for the alteration of an insulin-associated parameter, and further for prevention and/or treatment of a condition associated with insulin levels and/or insulin activity. The invention further relates to a composition comprising (i) ghrelin and/or an analog thereof and (ii) unacylated ghrelin and/or an analog thereof. In embodiments, the invention relates to a use of the composition for the alteration of an insulin-associated parameter, and further for prevention and/or treatment of a condition associated with insulin levels and/or insulin activity.

In an embodiment, the (i) ghrelin and/or analog thereof and (ii) unacylated ghrelin and/or analog thereof are administered to a subject at separate points or routes of administration. In a further embodiment, (i) and (ii) above are administered to a subject at substantially the same point or route of administration. In an embodiment (i) and (ii) above are administered to a subject sequentially. In an embodiment (i) and (ii) above are administered to a subject substantially simultaneously or simultaneously. In an embodiment either (i) or (ii) above or both are substantially pure. In an embodiment (i) and (ii) above are administered in substantially equal amounts relative to each other.

In an embodiment the (i) ghrelin and/or analog thereof and (ii) unacylated ghrelin and/or analog thereof are present together in a composition. In a further embodiment the composition further comprises a pharmaceutically acceptable carrier. In an embodiment, the composition comprises the (i) ghrelin and/or analog thereof and (ii) unacylated ghrelin and/or analog thereof in substantially equal amounts relative to each other.

In an embodiment, the condition associated with or related to insulin levels and/or activity is insulin resistance. In embodiments, the insulin resistance is associated with a state or condition chosen from the postprandial state, reduced GH levels and/or activity, obesity, diabetes (type I or type II), state of intravenous nutrition (e.g. due to critical illness), metabolic syndrome X or any combination of the above.

"Reduced GH levels and/or activity" as used herein refers to a GH level or activity which is reduced relative to normal amounts seen in healthy individuals or relative to higher GH states seen for example during different times of the day or following different activities or treatments. In embodiments such reduced levels are associated with a condition chosen from obesity, pituitary gland deficiency (e.g. caused by disease, trauma or surgical removal or other loss of tissue), or intravenous nutrition (e.g. due to critical illness). GH levels are also reduced during aging, for example, a normal teenager may produce about 700 μg/day of GH while a normal adult may produce about 400 μg/day of GH (Basic and Clinical Endocrinology [Lange Series], 2000, Appleton and Lange).

In an embodiment, the subject noted above is a mammal, in a further embodiment, a human.

In an embodiment, the forms of ghrelin (or an analog thereof) and/or unacylated ghrelin (or an analog thereof) are mammalian forms, in a further embodiment, human forms.

In an embodiment, the subject suffers from a GH deficiency.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

Throughout this application, various references are referred to describe more fully the state of the art to which this invention pertains. The disclosures of these references are hereby incorporated by reference into the present disclosure.

EXAMPLES

Example 1

Methods

Subjects

Eight male subjects with a pituitary insufficiency but otherwise healthy, were asked to participate (range 21-69 yrs (age 55±10; mean±standard error of mean or SEM)) and a body mass index of 29.4±2.8 (mean±SEM). All were treated by trans-sphenoidal surgery at least two years before enrolment for non-functioning pituitary tumors and all were on stable replacement therapy for their pituitary dependent thyroidal, adrenal and gonadal insufficiency, including GH therapy for at least more than 1 year and all had a serum total IGF-I concentration within the age and sex adjusted normal range. All subjects were admitted at the Clinical Research Unit. No alcoholic beverages were allowed from the day prior to admission until the end of the study. Also, all subjects were asked to skip the administration of their GH replacement every night prior to each of the 5 admission days. All subjects gave their written informed consent to participate in the study, which had been approved the hospital's Ethical Committee.

All subjects underwent the following five testing sessions, each after an overnight fast, in random order and at least 1 week apart: 1) placebo (saline 3 ml iv). 2) acylated ghrelin (Neosystem S.A.; Strasbourg, France; 1.0 μg/kg iv, using a bacterial filter system). 3) unacylated ghrelin (Neosystem S.A.; Strasbourg, France; 1.0 μg/kg iv, using a filter system). 4) acylated ghrelin (1.0 μg/kg iv) but this time after the normal GH replacement dose was administered 15 minutes before. 5) acylated ghrelin in combination with unacylated ghrelin (both 1.0 μg/kg iv, but via separate injection sites). All tests started in the morning at 09:30 am, 30' after one or two indwelling catheters had been placed into an antecubital vein, kept patent by slow infusion of isotonic saline.

After the administration at 10:00 am of AG, or the combination of UAG and AG, blood samples were collected for two hours, after which a standard meal is given (i.e. two hours after the administration) that existed of two slices of bread with butter and preservative, along with a glass of milk. This meal was taken by all subjects all tests days.

Assessments

Insulin was assessed with a radioimmunoassay (Medgenix Diagnostics, Brussels, Belgium; intra- and interassay coefficient of variation (CV) 13.7 and 8.0% respectively). Glucose was assessed with an automatic hexokinase method (Roche, Almere, The Netherlands). Free fatty acids were determined with an enzymatic calorimetric method (Wako Chemicals GmbH, Neuss, Germany; intra- and interassay CV 1.1 and 4.1% respectively).

Acylated and total ghrelin concentrations were measured, using a commercially available radioimmunoassay (Linco research Inc. Missouri, USA). This assay utilizes an antibody, which is specific for ghrelin with the n-octanoyl group on Serine-3. The Linco Ghrelin (Active) assay utilizes $^{125}$I-labeled Ghrelin and ghrelin antiserum to determine the level of active ghrelin in serum, plasma or tissue culture media by the double antibody/PEG technique. The lowest level of ghrelin that can be detected by this assay is 10 μg/ml when using a 100 μl sample size. Within and between assay variations of the acylated ghrelin assay are respectively 7 and 13%. The Linco total ghrelin assay within and between assay variations are respectively 5 and 15%.

Statistical Analyses

Differences between the several study days were calculated, using a Newman-Keuls Multiple Comparison one-way ANOVA test (GraphPad Prism 4 for Windows; GraphPad Inc. USA). P-values <0.05 were considered significant. Areas under the curve were calculated using the trapezoid rule.

Example 2

Results

Ghrelin Levels

The intravenous administration of 1 μg/kg AG only induces a relative small peak in AG levels in serum, which disappeared within two hours. Apparently, most of the AG was almost immediately degraded into UAG (see FIG. 1). However, as shown in Table 1, the total ghrelin concentration after administration of AG is significantly higher than when UAG was administered (P<0.05). Moreover, total ghrelin levels after injection of UAG+AG were not significantly higher than after AG administration, but were significantly higher after the injection of UAG alone (Table 1 and FIG. 2).

TABLE 1

Total ghrelin concentrations the first two hours following an injection of 1 μg/kg acylated ghrelin (AG), 1 μg/kg unacylated ghrelin (UAG) and/or growth hormone (GH; normal replacement dose) in 6 GH deficient subjects after an overnight fast. If P < 0.05, the first compound mentioned reflects the lowest results in concentrations per row.

| Injected compounds | P value |
|---|---|
| UAG versus AG + UAG | P < 0.01 |
| UAG versus AG + GH | P > 0.05 |
| UAG versus AG | P < 0.05 |
| AG versus AG + UAG | P > 0.05 |
| AG versus AG + GH | P > 0.05 |
| AG + GH versus AG + UAG | P > 0.05 |

Figure 4:
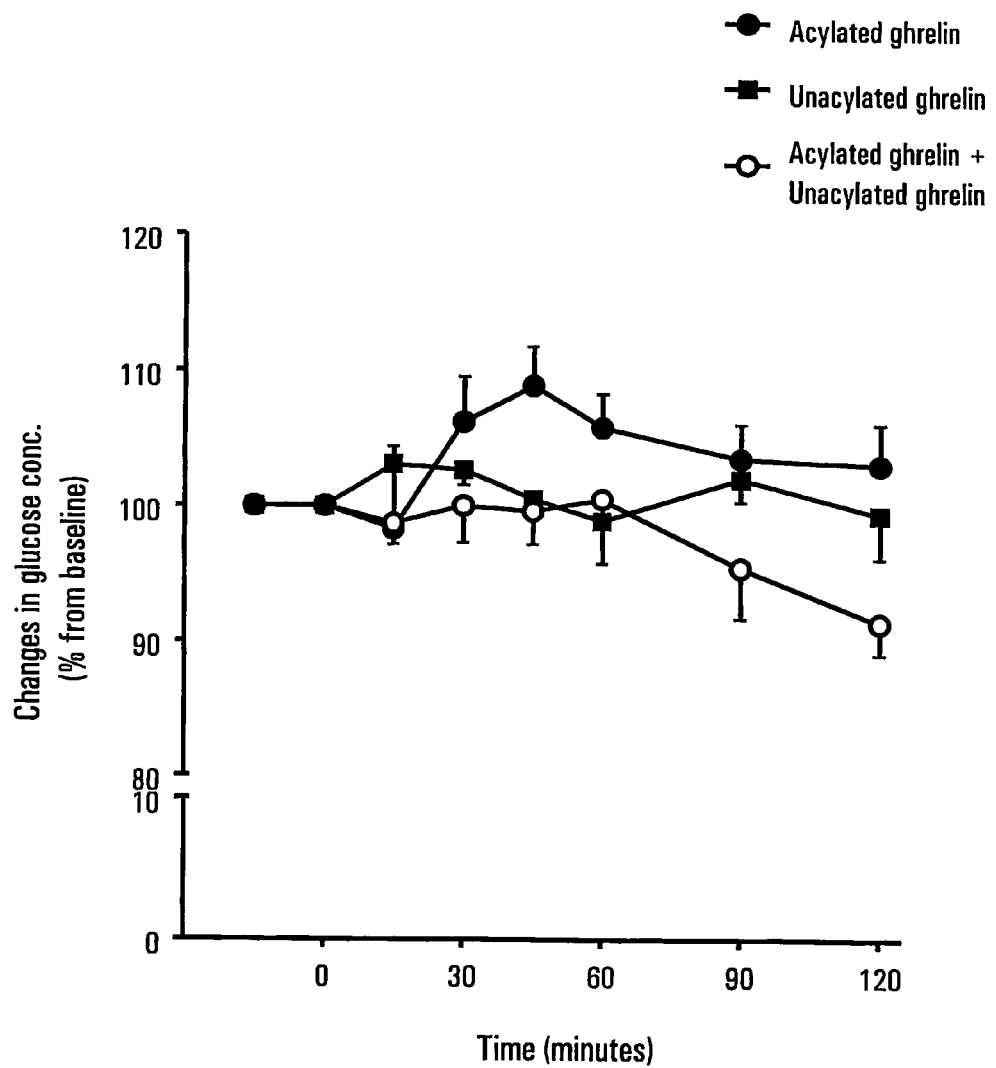
FIG. 4: Serum glucose concentrations as % of baseline after an i.v. bolus injection of 1 µg/kg acylated ghrelin (●), 1 µg/kg unacylated ghrelin (■) or the combination of 1 µg/kg acylated ghrelin and 1 µg/kg unacylated ghrelin (○) in 6 GH deficient subjects after an overnight fast.
Figure 5A:
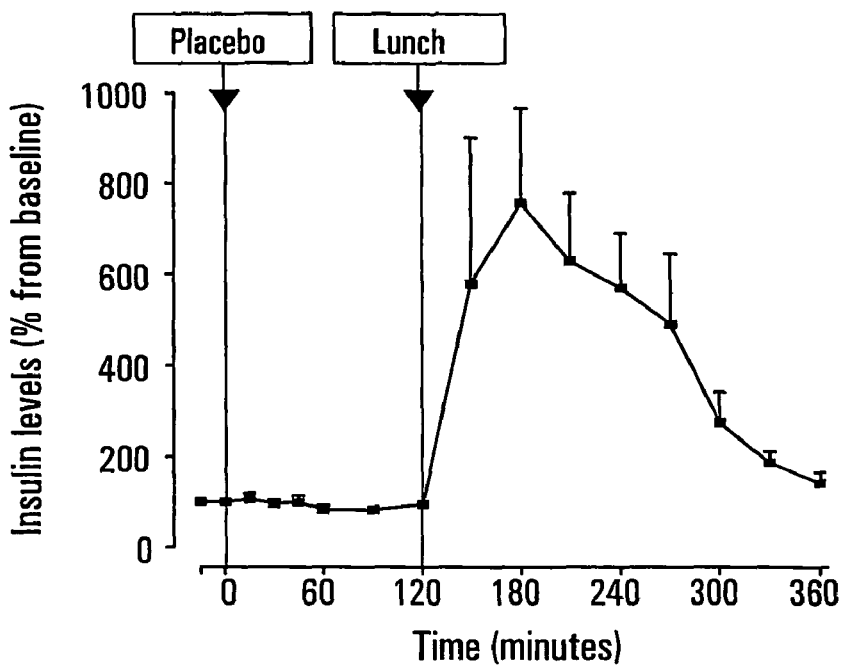
FIGS. 5A-5E: Changes in serum insulin concentrations as % of baseline in 6 GH deficient subjects after administration of (A) placebo, (B) AG and GH, (C) AG only, (D) UAG only and (E) AG and UAG. AG=acylated ghrelin (1 µg/kg i.v.); UAG=unacylated ghrelin (1 µg/kg i.v.); GH=growth hormone (normal daily replacement dose).
Figure 5B:
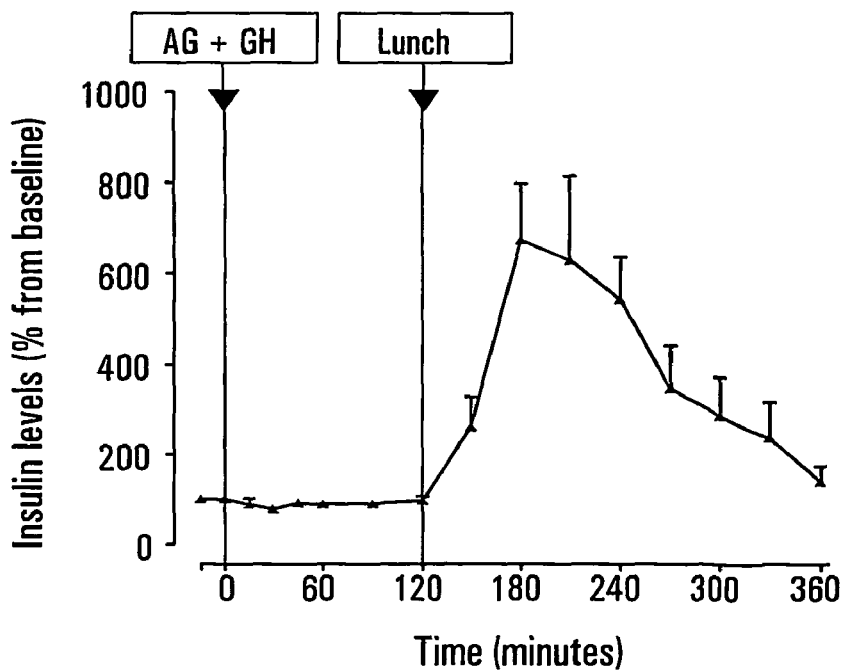
Figure 5C:
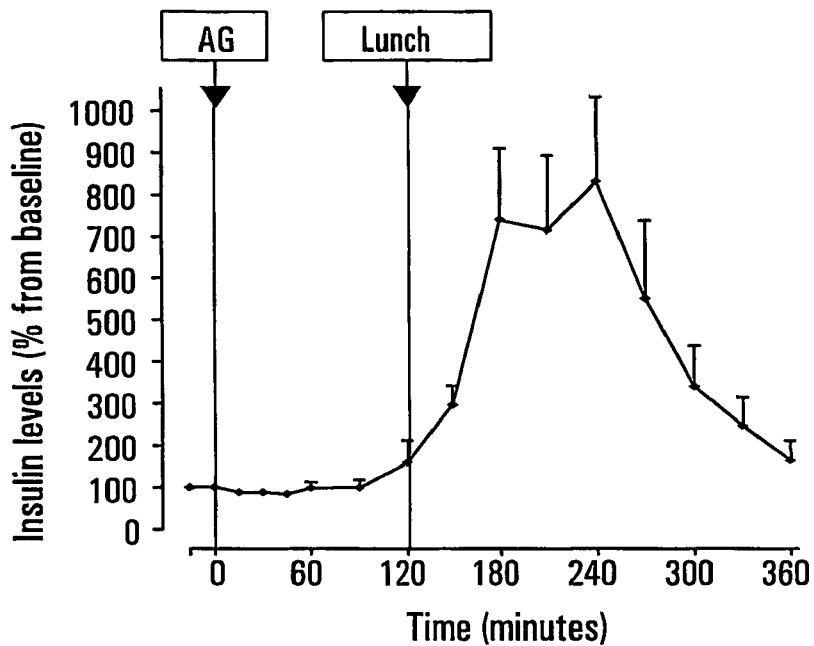
Figure 5D:
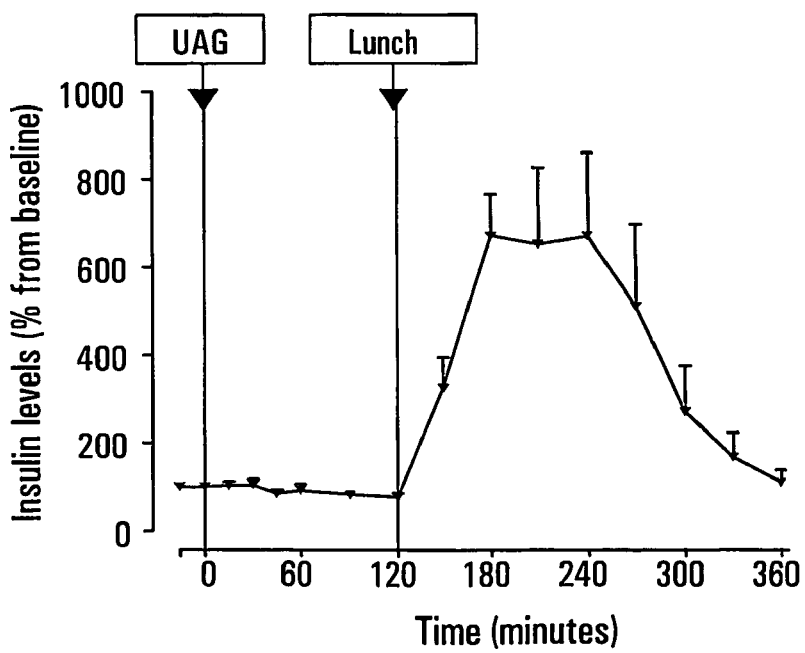
Figure 5E:
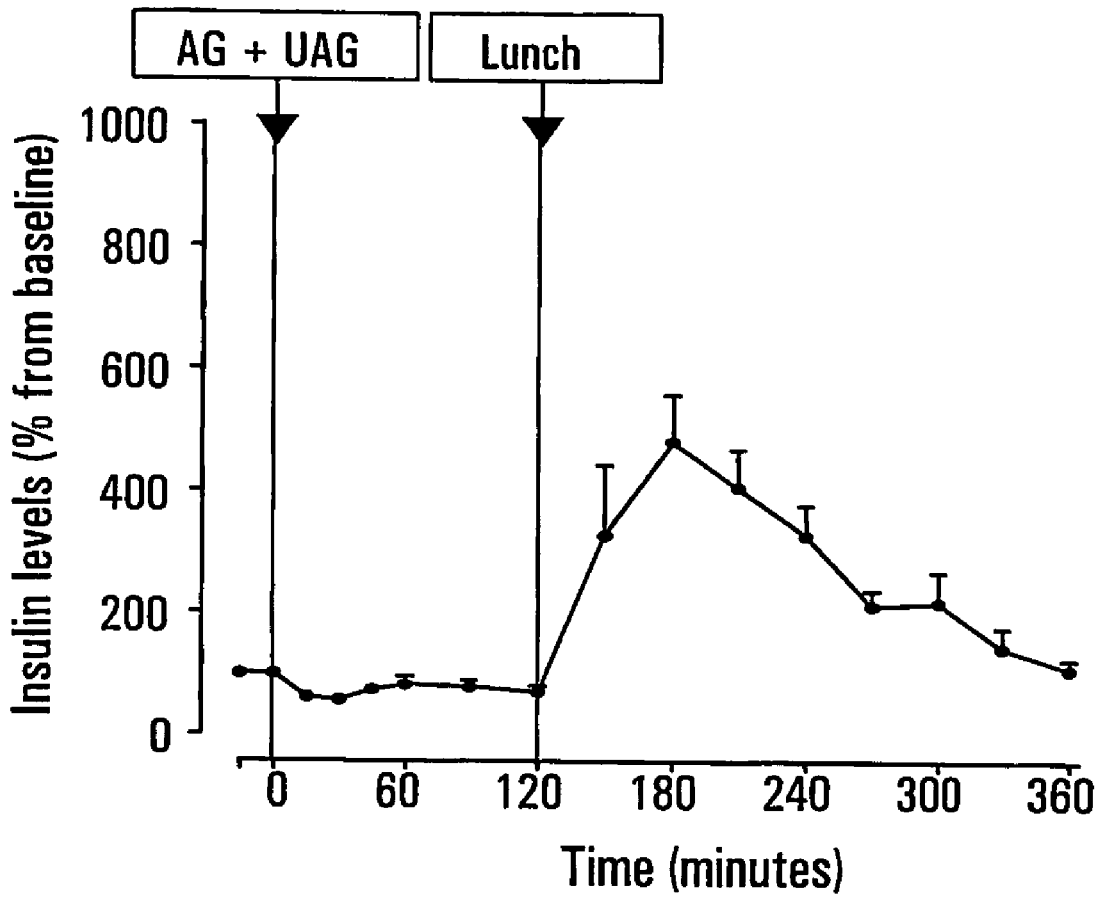

FIGS. 3 and 4 show the serum glucose levels after administration of placebo, AG (with or without the presence of GH) and UAG, alone or together with AG, while Table 2 shows the changes in glucose levels the first two hours after administration, but before lunch, so when these GH deficient subjects were still fasting. The administration of AG and, to a lesser extent, UAG, induces a significant hyperglycemia. When GH is administered 15' prior to the administration of AG, this hyperglycemia does not occur, which is also true when AG and UAG are given simultaneously.

TABLE 2

Analyses of differences between serum glucose concentrations the first two hours following an intravenous injection of 1 µg/kg acylated ghrelin (AG), 1 µg/kg unacylated ghrelin (UAG) and/or growth hormone (GH; normal replacement dose) in 6 GH deficient subjects after an overnight fast. If $P < 0.05$, the first compound mentioned reflects the lowest results in concentrations per row.

| Injected compounds | P value |
| --- | --- |
| Placebo versus AG | $P < 0.001$ |
| Placebo versus UAG | $P < 0.05$ |
| Placebo versus AG + GH | $P > 0.05$ |
| Placebo versus AG + UAG | $P > 0.05$ |
| AG + UAG versus AG | $P < 0.01$ |
| AG + UAG versus UAG | $P > 0.05$ |
| AG + GH versus AG + UAG | $P > 0.05$ |
| AG + GH versus AG | $P < 0.01$ |
| AG + GH versus UAG | $P > 0.05$ |
| AG versus UAG | $P > 0.05$ |

FIG. 3 and Table 3 show that the administration of AG and UAG still changes serum glucose levels after a standard lunch. Both AG and UAG increase serum glucose levels significantly in these GH deficient subjects (P<0.001). However, when AG is given after the administration of the normal replacement dose of GH, These changes in serum glucose levels after lunch can no longer be observed. The combination of AG+UAG seem to lower serum glucose levels significantly, when compared to the changes in glucose as seen after AG or UAG administration. Finally, UAG increases serum glucose levels significantly more than AG (P<0.01).

TABLE 3

Analyses of differences between serum glucose concentrations the first 4 hours after a standard lunch, which was 4 hours after injection of 1 µg/kg acylated ghrelin (AG), 1 µg/kg unacylated ghrelin (UAG) and/or growth hormone (GH; normal replacement dose) in 6 GH deficient subjects. If $P < 0.05$, the first compound mentioned reflects the lowest results in concentrations per row.

| Injected compounds | P value |
| --- | --- |
| AG + UAG versus UAG | $P < 0.001$ |
| AG + UAG versus AG | $P < 0.001$ |
| AG + UAG versus AG + GH | $P > 0.05$ |
| AG + UAG versus Placebo | $P > 0.05$ |
| Placebo versus UAG | $P < 0.001$ |
| Placebo versus AG | $P < 0.001$ |
| Placebo versus AG + GH | $P > 0.05$ |
| AG + GH versus UAG | $P < 0.001$ |
| AG + GH versus AG | $P < 0.001$ |
| AG versus UAG | $P < 0.01$ |

Insulin Levels

Figure 6:
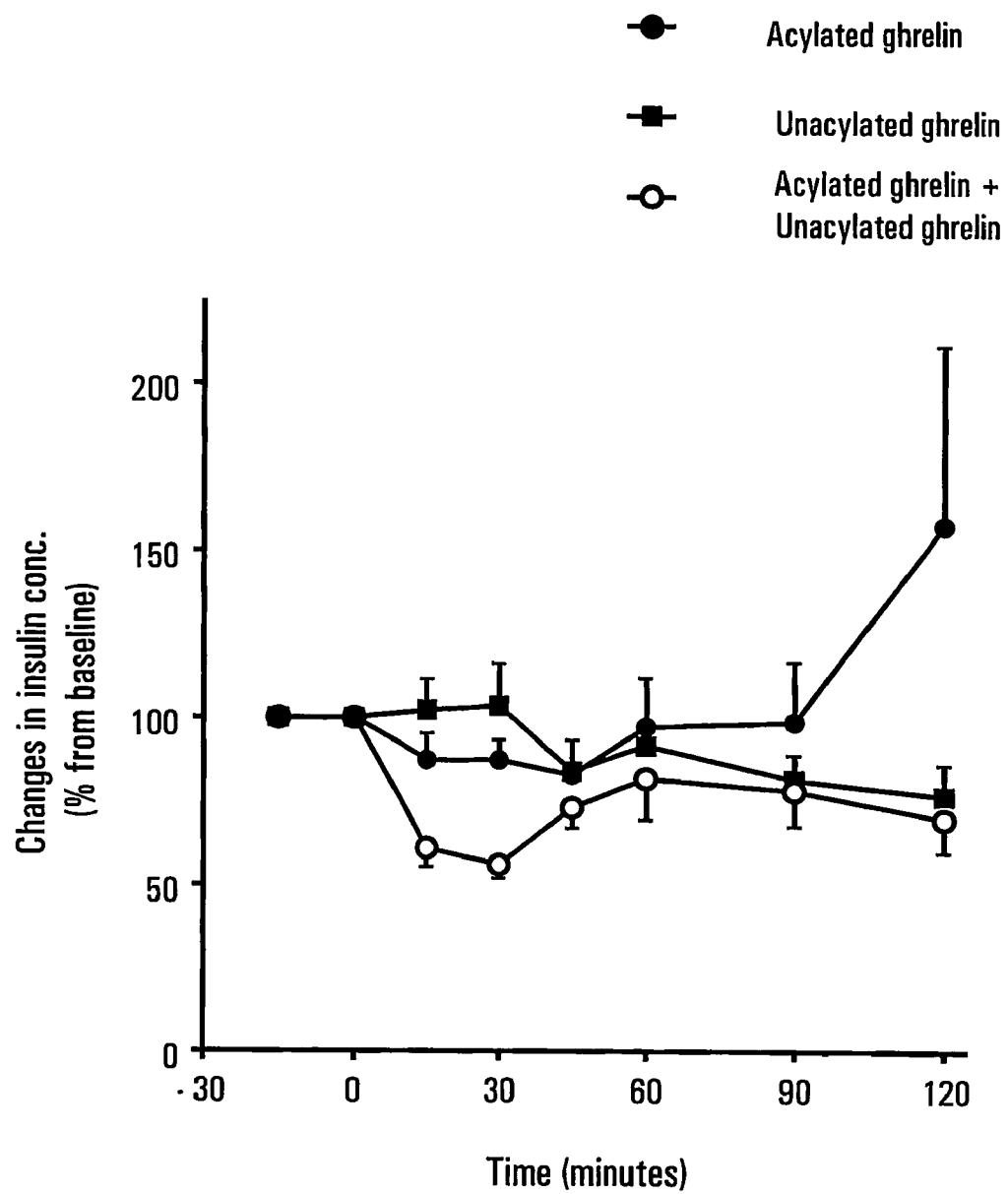
FIG. 6: Serum insulin concentrations as % of baseline after an i.v. bolus injection of 1 µg/kg acylated ghrelin (●), 1 µg/kg unacylated ghrelin (■) or the combination of 1 µg/kg acylated ghrelin and 1 µg/kg unacylated ghrelin (○) in 6 GH deficient subjects after an overnight fast.
Figure 7A:
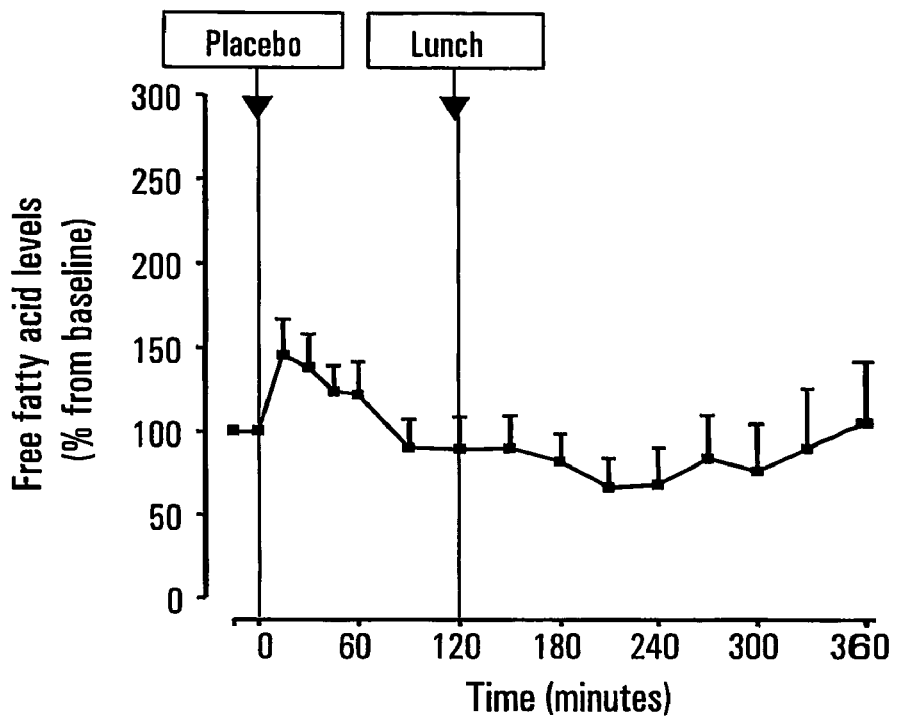
FIGS. 7A-7E: Changes in serum free fatty acid concentrations as % of baseline in 6 GH deficient subjects after administration of (A) placebo, (B) AG and GH, (C) AG only, (D) UAG only and (E) AG and UAG. AG=acylated ghrelin (1 µg/kg i.v.); UAG=unacylated ghrelin (1 µg/kg i.v.); GH growth hormone (normal daily replacement dose).
Figure 7B:
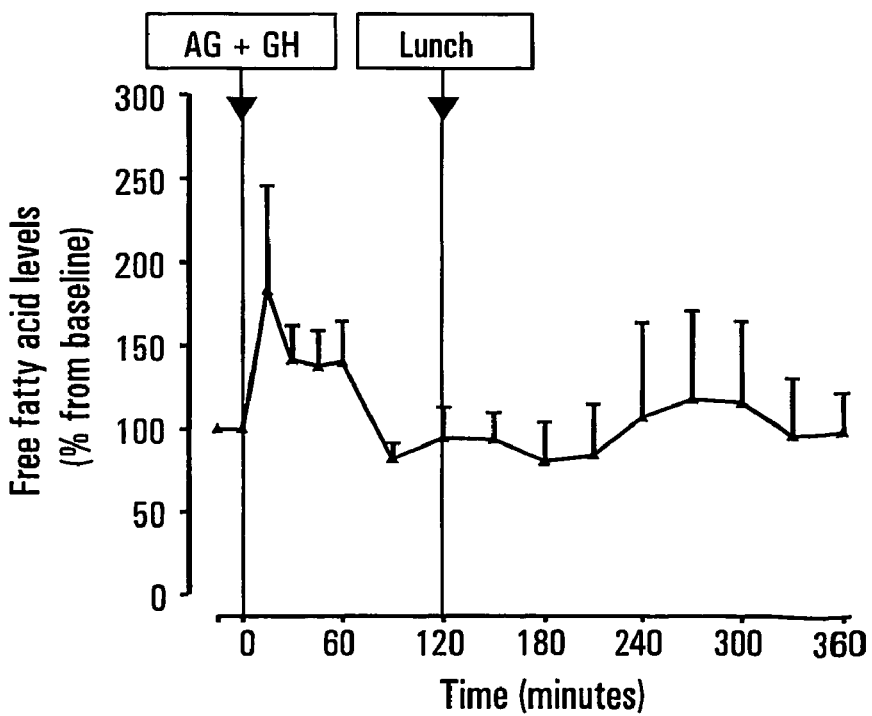
Figure 7C:
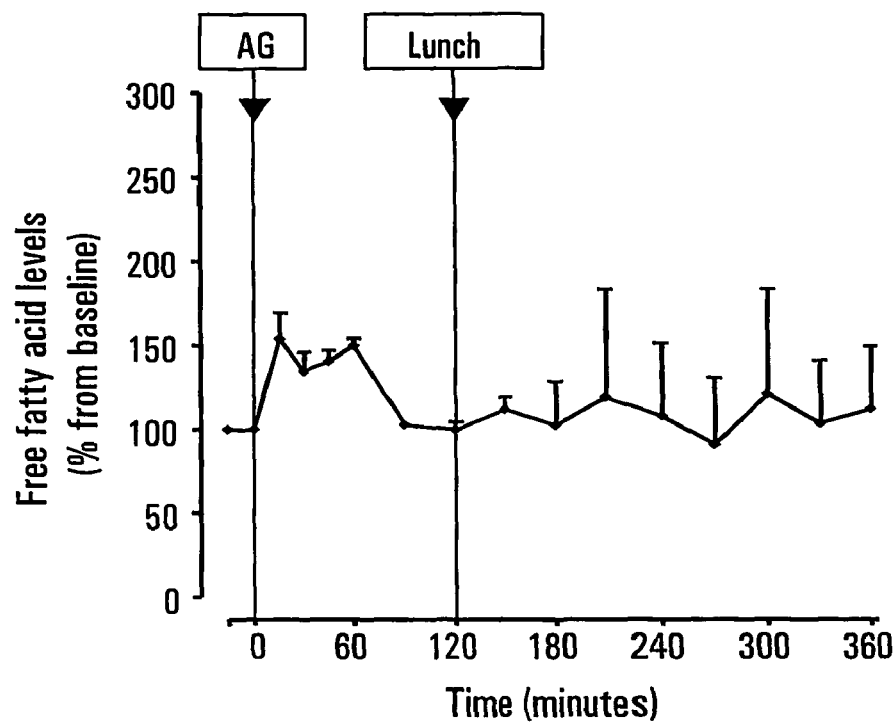
Figure 7D:
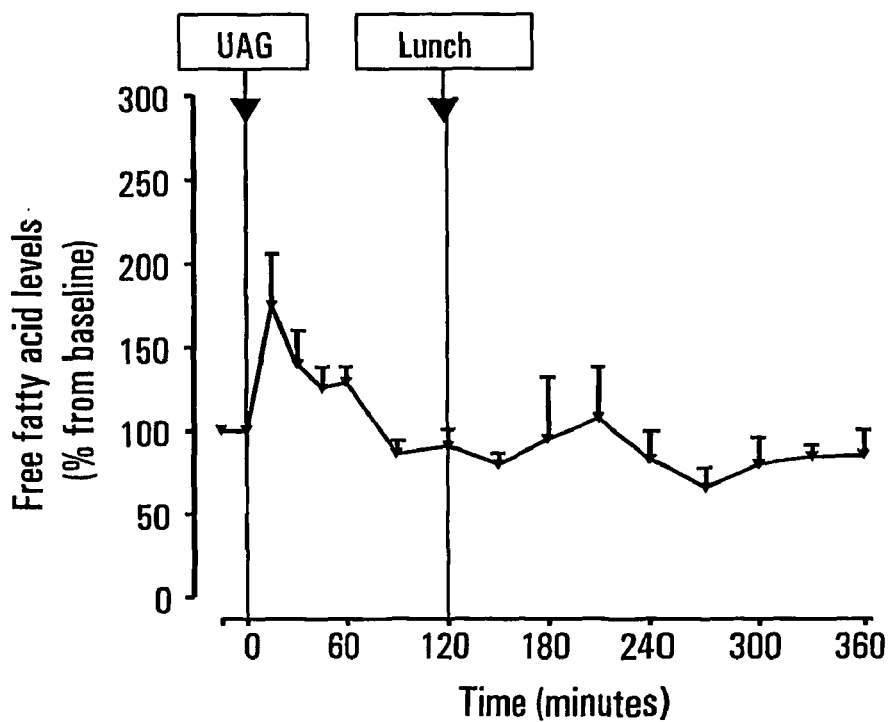
Figure 7E:
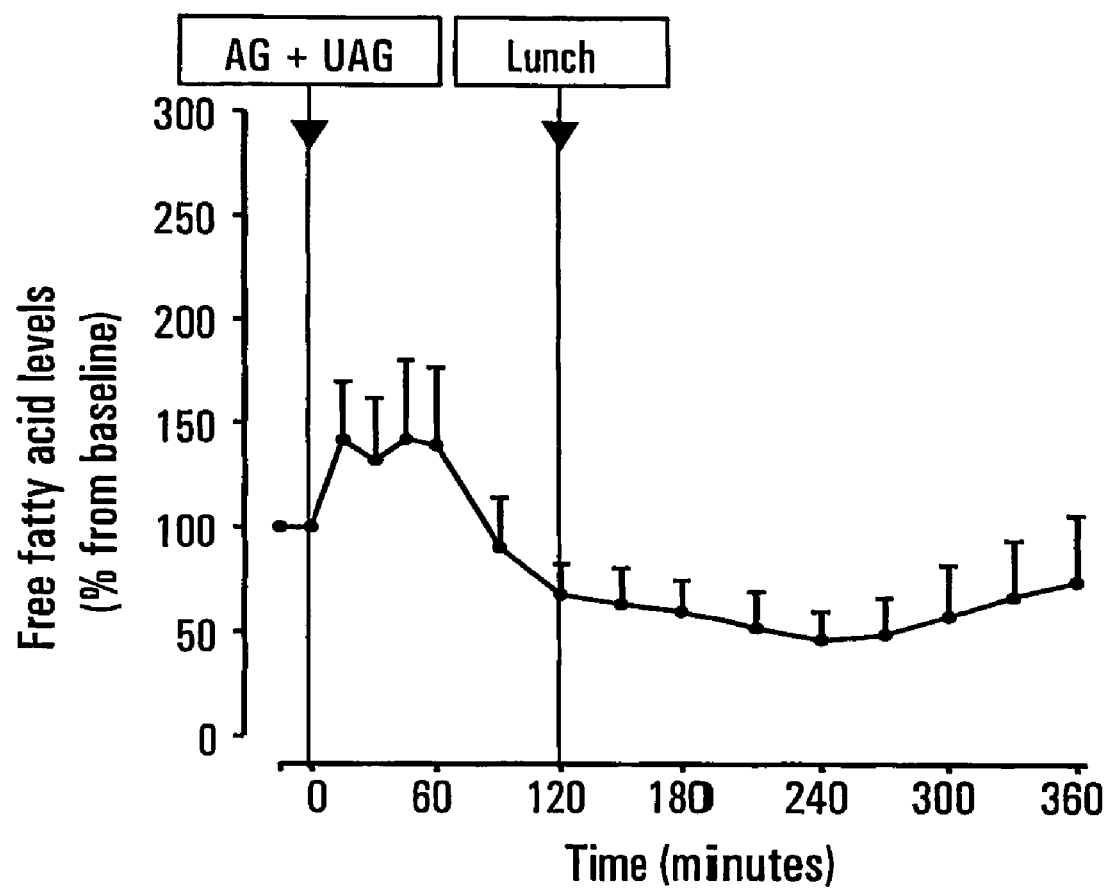

FIGS. 5 and 6 show the serum insulin levels after administration of placebo, AG (with or without the presence of GH) and UAG, alone or together with AG, while Table 4 shows the changes in insulin levels the first two hours after administration, but before lunch, so when these GH deficient subjects were still fasting. The administration of AG+UAG induces a significant reduction in serum insulin levels (p<0.05). All other interventions did not significantly change serum insulin levels the first two hours after administration.

TABLE 4

Analyses of differences between serum insulin concentrations the first two hours following an injection of 1 µg/kg acylated ghrelin (AG), 1 µg/kg unacylated ghrelin (UAG) and/or growth hormone (GH; normal replacement dose) in 6 GH deficient subjects after an overnight fast. If $P < 0.05$, the first compound mentioned reflects the lowest results in concentrations per row.

| Injected compounds | P value |
| --- | --- |
| AG + UAG versus AG | $P < 0.05$ |
| AG + UAG versus Placebo | $P > 0.05$ |
| AG + UAG versus UAG | $P > 0.05$ |
| AG + UAG versus AG + GH | $P > 0.05$ |
| AG + GH versus AG | $P > 0.05$ |
| AG + GH versus Placebo | $P > 0.05$ |
| AG + GH versus UAG | $P > 0.05$ |
| UAG versus AG | $P > 0.05$ |
| UAG versus Placebo | $P > 0.05$ |
| Placebo versus AG | $P > 0.05$ |

FIG. 5 and Table 5 show that the administration of AG and UAG impressively reduces serum insulin levels after a standard lunch (p<0.001). The serum insulin levels after lunch when AG was given together with UAG were significantly lower than observed after the administration of placebo, and after AG (with or without GH) or UAG alone. Also, AG, with or without the presence of GH increased insulin levels the most, followed UAG.

TABLE 5

Analyses of differences between serum insulin concentrations the first 4 hours after a standard lunch, which was 4 hours after injection of 1 µg/kg acylated ghrelin (AG), 1 µg/kg unacylated ghrelin (UAG) and/or growth hormone (GH; normal replacement dose) in 6 GH deficient subjects. If $P < 0.05$, the first compound mentioned reflects the lowest results in concentrations per row.

| Injected compounds | P value |
| --- | --- |
| AG + UAG versus AG | $P < 0.001$ |
| AG + UAG versus Placebo | $P < 0.01$ |
| AG + UAG versus UAG | $P < 0.01$ |
| AG + UAG versus AG + GH | $P < 0.05$ |
| AG + GH versus AG | $P > 0.05$ |
| AG + GH versus Placebo | $P > 0.05$ |
| AG + GH versus UAG | $P > 0.05$ |
| UAG versus AG | $P > 0.05$ |
| UAG versus Placebo | $P > 0.05$ |
| Placebo versus AG | $P > 0.05$ |

Free Fatty Acid Levels

FIG. 7 shows the serum FFA levels after administration of placebo, AG (with or without the presence of GH) and UAG, alone or together with AG. There were significant differences in FFA levels between the several observations during the first two hours, when subjects were still fasting. The administration of any compound, including placebo, induced an increase in FFA concentrations.

FIG. 7 and Table 6 show that the administration of AG and UAG impressively reduces serum FFA levels, compared to placebo, AG (with or without GH) and UAG, after a standard lunch (p<0.001 for all comparisons). AG (with or without GH), administered 2-6 hrs before, significantly increased FFA levels after lunch, compared to placebo; something that could not be observed when UAG was administered. For a comparison, the base line parameters of these metabolites were given in Table 7.

TABLE 6

Analyses of differences between serum free fatty acid concentrations the first 4 hours after a standard lunch, which was 4 hours after injection of 1 μg/kg acylated ghrelin (AG), 1 μg/kg unacylated ghrelin (UAG) and/or growth hormone (GH; normal replacement dose) in 6 GH deficient subjects. If $P < 0.05$, the first compound mentioned reflects the lowest results in concentrations per row.

| Injected compounds | P value |
|---|---|
| AG + UAG versus AG | $P < 0.001$ |
| AG + UAG versus AG + GH | $P < 0.001$ |
| AG + UAG versus UAG | $P < 0.001$ |
| AG + UAG versus Placebo | $P < 0.001$ |
| Placebo versus AG | $P < 0.01$ |
| Placebo versus AG + GH | $P < 0.05$ |
| Placebo versus UAG | $P > 0.05$ |
| UAG versus AG | $P < 0.01$ |
| UAG versus AG + GH | $P < 0.05$ |
| AG + GH versus AG | $P > 0.05$ |

TABLE 7

Baseline levels of main parameters. Concentrations were within the normal range in all subjects.

| Fasting concentrations at baseline | Mean ± SEM |
|---|---|
| Glucose (mmol/l) | 5.6 ± 0.16 |
| Insulin (pmol/l) | 196 ± 37 |
| Free fatty acids (mmol/l) | 0.94 ± 0.09 |

Figure 8:
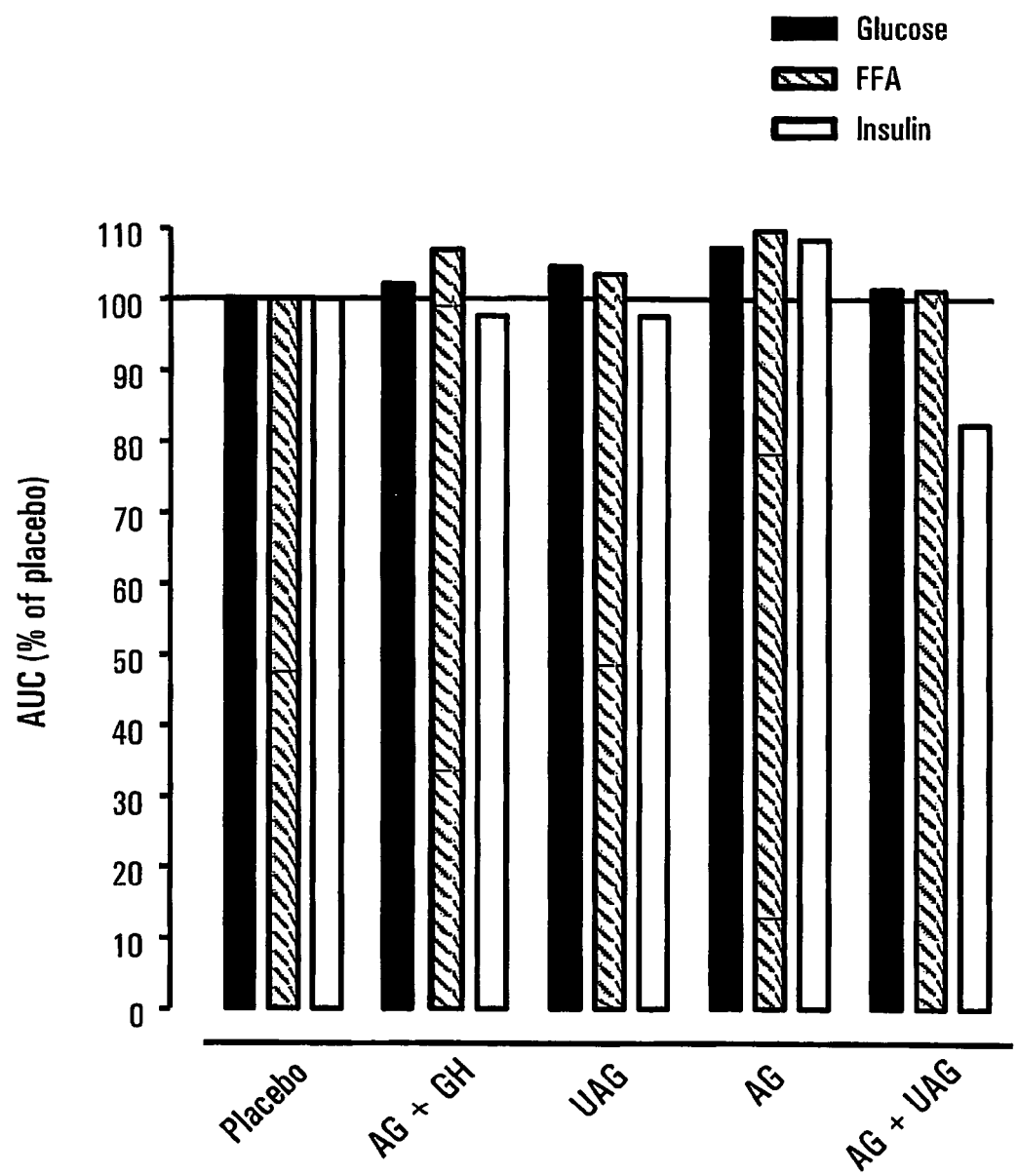
FIG. 8: Changes in areas under the curve of serum glucose, insulin and free fatty acid concentrations as % of baseline in 6 GH deficient subjects during first 2 hrs after the intravenous administration of placebo, AG (with or without GH), UAG and AG+UAG. AG=acylated ghrelin (1 µg/kg i.v.); UAG=unacylated ghrelin (1 µg/kg i.v.); GH=growth hormone (normal daily replacement dose).
Figure 9:
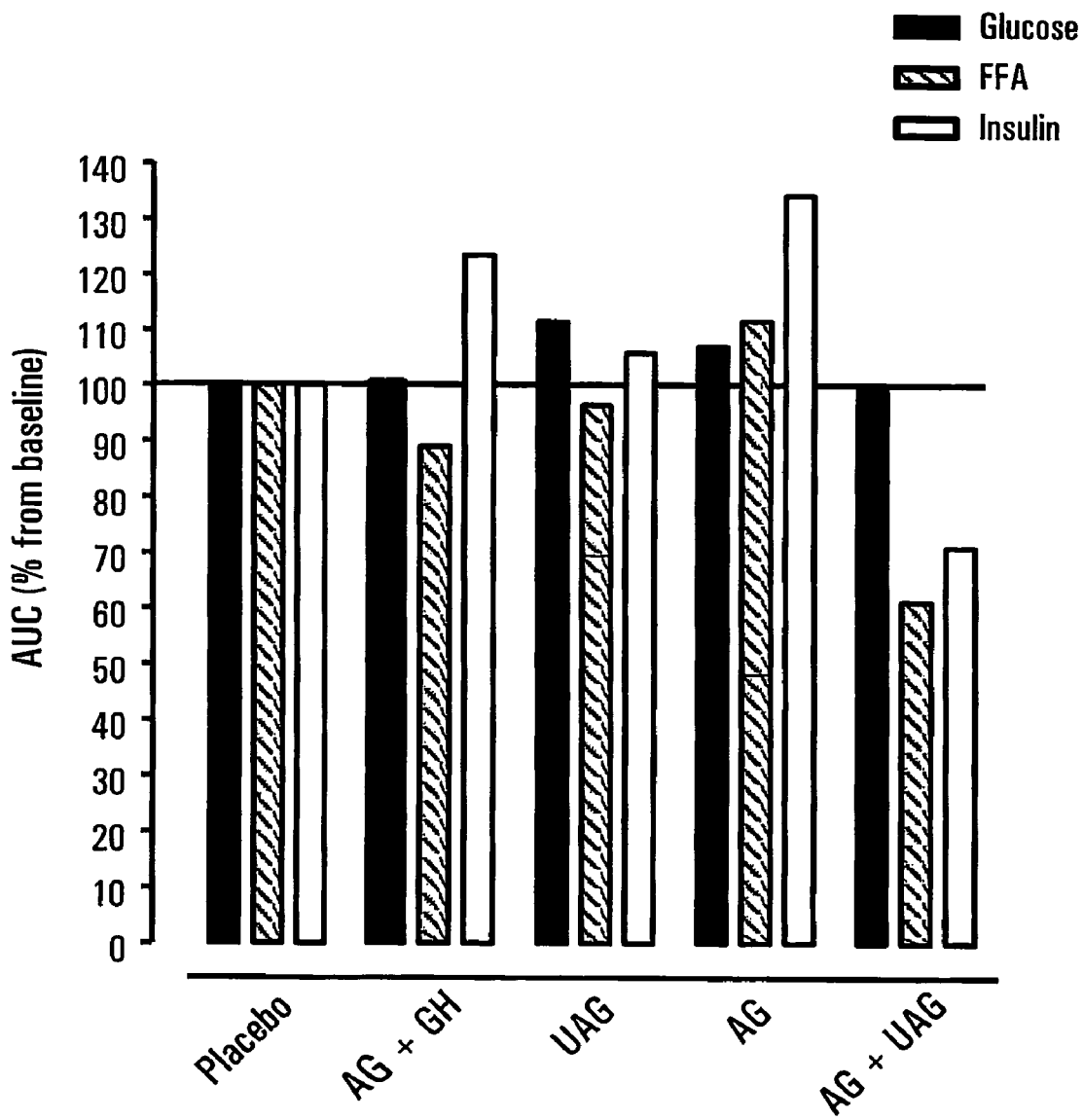
FIG. 9: Changes in areas under the curve of serum glucose, insulin and free fatty acid concentrations as % of baseline in 6 GH deficient subjects during first 4 hrs after lunch after the intravenous administration of placebo, AG (with or without GH), UAG and AG+UAG. AG=acylated ghrelin (1 µg/kg i.v.); UAG=unacylated ghrelin (1 µg/kg i.v.); GH=growth hormone (normal daily replacement dose).

FIG. 8 shows the glucose, insulin and FFA levels, in the first two hours following the administration of AG (with or without GH), UAG and the combination of AG+UAG, expressed as areas under the curve (AUC). The combination of AG+UAG improves insulin sensitivity. FIG. 9 shows the same parameters as AUC, but for the period following lunch. FIG. 9 demonstrates that AG decreases insulin sensitivity, compared to placebo, but it also shows that again the combination of AG and UAG impressively improves insulin sensitivity, which is also translated into the lower FFA levels in this situation.

It is shown herein that administration, e.g. by intravenous bolus injection, of acylated ghrelin is almost immediately degraded, but it also immediately increases glucose and insulin levels. This does not occur when unacylated ghrelin is injected, and moreover, unacylated ghrelin can prevent these effects of acylated ghrelin when it is co-injected with it. Also, acylated ghrelin induces an acute increase in unacylated ghrelin levels, most likely via a decrease in the clearance of ghrelin. Finally, acylated ghrelin can induce a decrease in insulin sensitivity up to at least 6 hours after administration, which again can be prevented or even actively improved by co-injection of unacylated ghrelin. These data indicate that the ghrelin system, using both the acylated and unacylated molecules, is involved in the acute and long-term control of glucose metabolism and insulin sensitivity in humans, and thus provides a therapeutic approach for conditions in which insulin sensitivity is altered or disturbed.

REFERENCES

1. Kojima, M., Hosoda, H., Date, Y., Nakazato, M., Matsuo, H., and Kangawa, K. 1999. Ghrelin is a growth-hormone-releasing acylated peptide from stomach. Nature 402:656-660.
2. Tena-Sempere, M., Barreiro, M. L., Gonzalez, L. C., Gaytan, F., Zhang, F. P., Caminos, J. E., Pinilla, L., Casanueva, F. F., Dieguez, C., and Aguilar, E. 2002. Novel expression and functional role of ghrelin in rat testis. Endocrinology 143:717-725.
3. Date, Y., Kojima, M., Hosoda, H., Sawaguchi, A., Mondal, M. S., Suganuma, T., Matsukura, S., Kangawa, K., and Nakazato, M. 2000. Ghrelin, a novel growth hormone-releasing acylated peptide, is synthesized in a distinct endocrine cell type in the gastrointestinal tracts of rats and humans. Endocrinology 141:4255-4261.
4. Mori, K., Yoshimoto, A., Takaya, K., Hosoda, K., Ariyasu, H., Yahata, K., Mukoyama, M., Sugawara, A., Hosoda, H., Kojima, M. et al. 2000. Kidney produces a novel acylated peptide, ghrelin. FEBS Lett. 486:213-216.
5. Gualillo, O., Caminos, J., Blanco, M., Garcia-Caballero, T., Kojima, M., Kangawa, K., Dieguez, C., and Casanueva, F. 2001. Ghrelin, a novel placental-derived hormone. Endocrinology 142:788-794.
6. Korbonits, M., Kojima, M., Kangawa, K., and Grossman, A. B. 2001. Presence of ghrelin in normal and adenomatous human pituitary. Endocrine. 14:101-104.
7. Volante, M., Papotti, M., Gugliotta, P., Migheli, A., and Bussolati, G. 2001. Extensive DNA fragmentation in oxyphilic cell lesions of the thyroid. J. Histochem. Cytochem. 49:1003-1011.
8. Muccioli, G., Tschop, M., Papotti, M., Deghenghi, R., Heiman, M., and Ghigo, E. 2002. Neuroendocrine and peripheral activities of ghrelin: implications in metabolism and obesity. Eur. J. Pharmacol. 440:235-254.
9. Hattori, N., Saito, T., Yagyu, T., Jiang, B. H., Kitagawa, K., and Inagaki, C. 2001. GH, GH receptor, GH secretagogue receptor, and ghrelin expression in human T cells, B cells, and neutrophils. J. Clin. Endocrinol. Metab 86:4284-4291.
10. Tanaka, M., Hayashida, Y., Nakao, N., Nakai, N., and Nakashima, K. 2001. Testis-specific and developmentally induced expression of a ghrelin gene-derived transcript that encodes a novel polypeptide in the mouse. Biochim. Biophys. Acta 1522:62-65.
11. Chapman, I. M., Hartman, M. L., Pezzoli, S. S., and Thorner, M. O. 1996. Enhancement of pulsatile growth hormone secretion by continuous infusion of a growth hormone-releasing peptide mimetic, L-692,429, in older adults—a clinical research center study. J. Clin. Endocrinol. Metab 81:2874-2880.
12. Volante, M., Fulcheri, E., AllIa, E., Cerrato, M., Pucci, A., and Papotti, M. 2002. Ghrelin expression in fetal, infant, and adult human lung. J. Histochem. Cytochem. 50:1013-1021.
13. Kamegai, J., Tamura, H., Shimizu, T., Ishii, S., Sugihara, H., and Wakabayashi, I. 2000. Central effect of ghrelin, an endogenous growth hormone secretagogue, on hypothalamic peptide gene expression. Endocrinology 141:4797-4800.
14. Masuda, Y., Tanaka, T., Inomata, N., Ohnuma, N., Tanaka, S., Itoh, Z., Hosoda, H., Kojima, M., and Kangawa, K. 2000. Ghrelin stimulates gastric acid secretion and motility in rats. Biochem. Biophys. Res. Commun. 276:905-908.
15. Tschop, M., Smiley, D. L., and Heiman, M. L. 2000. Ghrelin induces adiposity in rodents. Nature 407:908-913.
16. Wren, A. M., Small, C. J., Ward, H. L., Murphy, K. G., Dakin, C. L., Taheri, S., Kennedy, A. R., Roberts, G. H., Morgan, D. G., Ghatei, M. A. et al. 2000. The novel hypothalamic peptide ghrelin stimulates food intake and growth hormone secretion. Endocrinology 141:4325-4328.
17. Broglio, F., Arvat, E., Benso, A., Gottero, C., Muccioli, G., Papotti, M., Van Der Lely, A. J., Deghenghi, R., and Ghigo, E. 2001. Ghrelin, a natural GH secretagogue produced by the stomach, induces hyperglycemia and reduces insulin secretion in humans. J. Clin. Endocrinol. Metab 86:5083-5086.
18. Date, Y., Nakazato, M., Murakami, N., Kojima, M., Kangawa, K., and Matsukura, S. 2001. Ghrelin acts in the central nervous system to stimulate gastric acid secretion. Biochem. Biophys. Res. Commun. 280:904-907.
19. Kamegai, J., Tamura, H., Shimizu, T., Ishii, S., Sugihara, H., and Wakabayashi, I. 2001. Chronic central infusion of ghrelin increases hypothalamic neuropeptide Y and Agouti-related protein mRNA levels and body weight in rats. Diabetes 50:2438-2443.
20. Nagaya, N., Kojima, M., Uematsu, M., Yamagishi, M., Hosoda, H., Oya, H., Hayashi, Y., and Kangawa, K. 2001. Hemodynamic and hormonal effects of human ghrelin in healthy volunteers. Am. J. Physiol Regul. Integr. Comp Physiol 280:R1483-R1487.
21. Wren, A. M., Seal, L. J., Cohen, M. A., Brynes, A. E., Frost, G. S., Murphy, K. G., Dhillo, W. S., Ghatei, M. A., and Bloom, S. R. 2001. Ghrelin enhances appetite and increases food intake in humans. J. Clin. Endocrinol. Metab 86:5992.
22. Zhang, W., Chen, M., Chen, X., Segura, B. J., and Mulholland, M. W. 2001. Inhibition of pancreatic protein secretion by ghrelin in the rat. J. Physiol 537:231-236.
23. Tolle, V., Bassant, M. H., Zizzari, P., Poindessous-Jazat, F., Tomasetto, C., Epelbaum, J., and Bluet-Pajot, M. T. 2002. Ultradian rhythmicity of ghrelin secretion in relation with GH, feeding behavior, and sleep-wake patterns in rats. Endocrinology 143:1353-1361.
24. Okumura, H., Nagaya, N., Enomoto, M., Nakagawa, E., Oya, H., and Kangawa, K. 2002. Vasodilatory effect of ghrelin, an endogenous Peptide from the stomach. J. Cardiovasc. Pharmacol. 39:779-783.
25. Horvath, T. L., Diano, S., Sotonyi, P., Heiman, M., and Tschop, M. 2001. Minireview: ghrelin and the regulation of energy balance—a hypothalamic perspective. Endocrinology 142:4163-4169.
26. Inui, A. 2001. Ghrelin: an orexigenic and somatotrophic signal from the stomach. Nat. Rev. Neurosci. 2:551-560.
27. Furuse, M., Tachibana, T., Ohgushi, A., Ando, R., Yoshimatsu, T., and Denbow, D. M. 2001. Intracerebroventricular injection of ghrelin and growth hormone releasing factor inhibits food intake in neonatal chicks. Neurosci. Lett. 301:123-126.
28. Yoshihara, F., Kojima, M., Hosoda, H., Nakazato, M., and Kangawa, K. 2002. Ghrelin: a novel peptide for growth hormone release and feeding regulation. Curr. Opin. Clin. Nutr. Metab Care 5:391-395.
29. Bednarek, M. A., Feighner, S. D., Pong, S. S., McKee, K. K., Hreniuk, D. L., Silva, M. V., Warren, V. A., Howard, A. D., Van der Ploeg, L. H., and Heck, J. V. 2000. Structure-function studies on the new growth hormone-releasing peptide, ghrelin: minimal sequence of ghrelin necessary for activation of growth hormone secretagogue receptor 1a. J. Med. Chem. 43:4370-4376.
30. Matsumoto, M., Hosoda, H., Kitajima, Y., Morozumi, N., Minamitake, Y., Tanaka, S., Matsuo, H., Kojima, M., Hayashi, Y., and Kangawa, K. 2001. Structure-activity relationship of ghrelin: pharmacological study of ghrelin peptides. Biochem. Biophys. Res. Commun. 287:142-146.
31. Muccioli, G., Papotti, M., Locatelli, V., Ghigo, E., and Deghenghi, R. 2001. Binding of $^{125}$I-labeled ghrelin to membranes from human hypothalamus and pituitary gland. J. Endocrinol. Invest 24:RC7-RC9.
32. Date, Y., Nakazato, M., Hashiguchi, S., Dezaki, K., Mondal, M. S., Hosoda, H., Kojima, M., Kangawa, K., Arima, T., Matsuo, H. et al. 2002. Ghrelin is present in pancreatic alpha-cells of humans and rats and stimulates insulin secretion. Diabetes 51:124-129.
33. Volante, M., AllIa, E., Gugliotta, P., Funaro, A., Broglio, F., Deghenghi, R., Muccioli, G., Ghigo, E., and Papotti, M. 2002. Expression of ghrelin and of the GH secretagogue receptor by pancreatic islet cells and related endocrine tumors. J. Clin. Endocrinol. Metab 87:1300-1308.
34. Wierup, N., Svensson, H., Mulder, H., and Sundler, F. 2002. The ghrelin cell: a novel developmentally regulated islet cell in the human pancreas. Regul. Pept. 107:63-69.
35. Cummings, D. E., Purnell, J. Q., Frayo, R. S., Schmidova, K., Wisse, B. E., and Weigle, D. S. 2001. A preprandial rise in plasma ghrelin levels suggests a role in meal initiation in humans. Diabetes 50:1714-1719.
36. Toshinai, K., Mondal, M. S., Nakazato, M., Date, Y., Murakami, N., Kojima, M., Kangawa, K., and Matsukura, S. 2001. Upregulation of ghrelin expression in the stomach upon fasting, insulin-induced hypoglycemia, and leptin administration. Biochem. Biophys. Res. Commun. 281: 1220-1225.
37. Ariyasu, H., Takaya, K., Tagami, T., Ogawa, Y., Hosoda, K., Akamizu, T., Suda, M., Koh, T., Natsui, K., Toyooka, S. et al. 2001. Stomach is a major source of circulating ghrelin, and feeding state determines plasma ghrelin-like immunoreactivity levels in humans. J. Clin. Endocrinol. Metab 86:4753-4758.
38. Saad, M. F., Bernaba, B., Hwu, C. M., Jinagouda, S., Fahmi, S., Kogosov, E., and Boyadjian, R. 2002. Insulin regulates plasma ghrelin concentration. J. Clin. Endocrinol. Metab 87:3997-4000.
39. Pagotto, U., Gambineri, A., Vincennati, V., Heiman, M. L., Tschop, M., and Pasquali, R. 2002. Plasma ghrelin, obesity and the polycystic ovary syndrome: Correlation with insulin resistance and androgen levels. J. Clin. Endocrinol. Metab. 87:5625-5629.
40. Caixas, A., Bashore, C., Nash, W., Pi-Sunyer, F., and Laferrere, B. 2002. Insulin, unlike food intake, does not suppress ghrelin in human subjects. J. Clin. Endocrinol. Metab 87:1902.
41. Svensson, J., Lonn, L., Jansson, J. O., Murphy, G., Wyss, D., Krupa, D., Cerchio, K., Polyino, W., Gertz, B., Boseaus, I. et al. 1998. Two-month treatment of obese subjects with the oral growth hormone (GH) secretagogue MK-677 increases GH secretion, fat-free mass, and energy expenditure. J. Clin. Endocrinol. Metab 83:362-369.
42. Chapman, I. M., Pescovitz, O. H., Murphy, G., Treep, T., Cerchio, K. A., Krupa, D., Gertz, B., Polyino, W. J., Skiles, E. H., Pezzoli, S. S. et al. 1997. Oral administration of growth hormone (GH) releasing peptide-mimetic MK-677 stimulates the GH/insulin-like growth factor-I axis in selected GH-deficient adults. J. Clin Endocrinol. Metab 82:3455-3463.
43. Muller, A. F., Janssen, J. A., Hofland, L. J., Lamberts, S. W., Bidlingmaier, M., Strasburger, C. J., and van der Lely, A. J. 2001. Blockade of the growth hormone (GH) receptor unmasks rapid GH-releasing peptide-6-mediated tissue-specific insulin resistance. J. Clin. Endocrinol. Metab 86:590-593.
44. Nakagawa, E., Nagaya, N., Okumura, H., Enomoto, M., Oya, H., Ono, F., Hosoda, H., Kojima, M., and Kangawa, K. 2002. Hyperglycaemia suppresses the secretion of ghrelin, a novel growth-hormone-releasing peptide: responses to the intravenous and oral administration of glucose. Clin. Sci. (Lond) 103:325-328.
45. Lucidi, P., Murdolo, G., Di Loreto, C., De Cicco, A., Parlanti, N., Fanelli, C., Santeusanio, F., Bolli, G. B., and De Feo, P. 2002. Ghrelin is not necessary for adequate hormonal counterregulation of insulin-induced hypoglycemia. Diabetes 51:2911-2914.

What is claimed is:

1. A method of treating insulin resistance in a subject, said method comprising administering to said subject an effective amount of ghrelin or ghrelin having one or more conservative amino acid substitutions and unacylated ghrelin or unacylated ghrelin having one or more conservative amino acid substitutions.

2. The method of claim 1, wherein said method comprises administering to said subject a composition comprising ghrelin or ghrelin having one or more conservative amino acid substitutions and unacylated ghrelin or unacylated ghrelin having one or more conservative amino acid substitutions.

3. The method of claim 2, wherein said composition further comprises a pharmaceutically acceptable carrier.

4. The method of claim 2, wherein said method is for reducing insulin resistance in said subject.

5. The method of claim 4, wherein said insulin resistance is associated with obesity.

6. The method of claim 5, wherein said obesity is associated with reduced growth hormone level, activity, or both.

7. The method of claim 4, wherein said subject has type II diabetes.

8. The method of claim 1, wherein said insulin resistance is associated with obesity.

9. The method of claim 8, wherein said obesity is associated with reduced growth hormone level, activity, or both.

10. The method of claim 1, wherein said subject has type II diabetes.

11. The method of claim 1, wherein said administration of said ghrelin or ghrelin having one or more conservative amino acid substitutions and said unacylated ghrelin or unacylated ghrelin having one or more conservative amino acid substitutions is sequential.

12. The method of claim 1, wherein said administration of said ghrelin or ghrelin having one or more conservative amino acid substitutions and said unacylated ghrelin or unacylated ghrelin having one or more conservative amino acid substitutions is simultaneous.

13. The method of claim 1, wherein said ghrelin comprises an amino acid sequence as set forth in SEQ ID NO: 1.

14. The method of claim 1, wherein said unacylated ghrelin comprises an amino acid sequence as set forth in SEQ ID NO: 2.

15. The method of claim 1, wherein said ghrelin or ghrelin having one or more conservative amino acid substitutions and said unacylated ghrelin or unacylated ghrelin having one or more conservative amino acid substitutions is administered through a route selected from the group consisting of intravenous, oral, transdermal, subcutaneous, mucosal, intramuscular, intranasal, intrapulmonary, parenteral, intrarectal and topical.

16. The method of claim 1, wherein said ghrelin or ghrelin having one or more conservative amino acid substitutions is administered at a dose of about 1 µg/kg.

17. The method of claim 1, wherein said unacylated ghrelin or unacylated ghrelin having one or more conservative amino acid substitutions is administered at a dose of about 1 µg/kg.

18. The method of claim 1, wherein said subject is a mammal.

19. The method of claim 1, wherein said subject is human.

20. A method for lowering glucose level in a subject, said method comprising administering to said subject an effective amount of ghrelin or ghrelin having one or more conservative amino acid substitutions in combination with unacylated ghrelin or unacylated ghrelin having one or more conservative amino acid substitutions.

21. The method of claim 20, wherein said method comprises administering to said subject a composition comprising ghrelin or ghrelin having one or more conservative amino acid substitutions and unacylated ghrelin or unacylated ghrelin having one or more conservative amino acid substitutions.

22. The method of claim 20, wherein said administration of said ghrelin or ghrelin having one or more conservative amino acid substitutions and said unacylated ghrelin or unacylated ghrelin having one or more conservative amino acid substitutions is sequential.

23. The method of claim 20, wherein said administration of said ghrelin or ghrelin having one or more conservative amino acid substitutions and said unacylated ghrelin or unacylated ghrelin having one or more conservative amino acid substitutions is simultaneous.

24. The method of claim 20, wherein said ghrelin comprises an amino acid sequence as set forth in SEQ ID NO: 1.

25. The method of claim 20, wherein said unacylated ghrelin comprises an amino acid sequence as set forth in SEQ ID NO: 2.

26. The method of claim 20, wherein said ghrelin or ghrelin having one or more conservative amino acid substitutions and said unacylated ghrelin or unacylated ghrelin having one or more conservative amino acid substitutions is administered through a route selected from the group consisting of intravenous, oral, transdermal, subcutaneous, mucosal, intramuscular, intranasal, intrapulmonary, parenteral, intrarectal and topical.

27. The method of claim 20, wherein said ghrelin or ghrelin having one or more conservative amino acid substitutions is administered at a dose of about 1 µg/kg.

28. The method of claim 20, wherein said unacylated ghrelin or unacylated ghrelin having one or more conservative amino acid substitutions is administered at a dose of about 1 µg/kg.

* * * * *

UNITED STATES PATENT AND TRADEMARK OFFICE
CERTIFICATE OF CORRECTION

PATENT NO. : 7,825,090 B2
APPLICATION NO. : 10/595485
DATED : November 2, 2010
INVENTOR(S) : Ezio Ghigo et al.

Page 1 of 1

It is certified that error appears in the above-identified patent and that said Letters Patent is hereby corrected as shown below:

On the Title Page please correct item (73) to read:

--(73) Assignee: Alizé Pharma SAS, Écully (FR)--.

Signed and Sealed this
Fourth Day of January, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,825,090 B2 | |
| APPLICATION NO. | : 10/595485 | |
| DATED | : November 2, 2010 | |
| INVENTOR(S) | : Ghigo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 508 days.

Signed and Sealed this
Twenty-fifth Day of January, 2011

David J. Kappos
*Director of the United States Patent and Trademark Office*